(12) United States Patent
Demarest et al.

(10) Patent No.: US 7,484,860 B2
(45) Date of Patent: *Feb. 3, 2009

(54) COMBINATION WHITE LIGHT AND COLORED LED LIGHT DEVICE WITH ACTIVE INGREDIENT EMISSION

(75) Inventors: Scott W. Demarest, Caledonia, WI (US); Darren K. Robling, Racine, WI (US); Cory J. Nelson, Racine, WI (US); Jeffrey J. Wolf, Racine, WI (US); Scott D. Walter, Twin Lakes, WI (US); Steven B. Mineau, Racine, WI (US); Matthew Abbondanzio, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 92 days.

This patent is subject to a terminal disclaimer.

(21) Appl. No.: 11/553,127

(22) Filed: Oct. 26, 2006

(65) Prior Publication Data

US 2007/0086199 A1 Apr. 19, 2007

Related U.S. Application Data

(63) Continuation-in-part of application No. 11/426,055, filed on Jun. 23, 2006, now Pat. No. 7,318,659, which is a continuation-in-part of application No. 11/069,964, filed on Mar. 3, 2005, now Pat. No. 7,246,919, which is a continuation-in-part of application No. 10/561,822, filed on Apr. 25, 2006.

(60) Provisional application No. 60/549,154, filed on Mar. 3, 2004, provisional application No. 60/483,913, filed on Jul. 2, 2003.

(51) Int. Cl.
*F21V 33/00* (2006.01)

(52) U.S. Cl. .................. 362/253; 362/643; 362/96; 362/101

(58) Field of Classification Search .......... 362/253, 362/640, 644, 647, 653, 96, 101, 643
See application file for complete search history.

(56) References Cited

U.S. PATENT DOCUMENTS

| | | |
|---|---|---|
| 1,535,486 A | 4/1925 | Lundy |
| 1,565,500 A | 12/1925 | Ritter |
| 1,706,939 A | 3/1929 | Rosenthal |
| 1,732,707 A | 10/1929 | Winsboro |
| 1,920,599 A | 8/1933 | Schuh |
| 2,124,543 A | 7/1938 | Clyne |
| 2,143,246 A | 1/1939 | McGary |
| 2,372,371 A | 3/1945 | Eisner |
| 2,435,756 A | 2/1948 | Schlesinger |
| 2,468,164 A | 4/1949 | Brewster |
| 2,469,656 A | 5/1949 | Lienert |
| 2,535,802 A | 12/1950 | Libson |
| 2,694,771 A | 11/1954 | Cox |
| 2,741,812 A | 4/1956 | Tellier |
| 2,741,813 A | 4/1956 | Rubin |
| 2,757,278 A | 7/1956 | Cloud |
| 2,799,166 A | 7/1957 | Leftwich |
| 2,818,770 A | 1/1958 | Cilurzo |
| 2,931,880 A | 4/1960 | Yaffe |
| 3,080,624 A | 3/1963 | Weber, III |
| 3,119,565 A | 1/1964 | Nottingham |
| 3,377,126 A | 4/1968 | Nijland et al. |
| 3,760,179 A | 9/1973 | Addington, Jr. |
| 3,763,347 A | 10/1973 | Whitaker |
| 3,923,458 A | 12/1975 | Moran |
| 3,948,445 A | 4/1976 | Andeweg |
| 4,009,384 A | 2/1977 | Holland |
| 4,045,664 A | 8/1977 | Vrenken et al. |
| 4,184,099 A | 1/1980 | Lindauer et al. |
| 4,234,907 A | 11/1980 | Daniel |
| 4,346,059 A | 8/1982 | Spector |
| 4,391,781 A | 7/1983 | van Lit |
| 4,463,286 A | 7/1984 | Justice |
| 4,493,011 A | 1/1985 | Spector |
| 4,510,555 A | 4/1985 | Mori |
| 4,519,017 A | 5/1985 | Daniel |
| 4,544,592 A | 10/1985 | Spector |
| 4,549,250 A | 10/1985 | Spector |
| 4,561,043 A | 12/1985 | Thompson |

| | | | | | | |
|---|---|---|---|---|---|---|
| 4,579,717 | A | 4/1986 | Gyulay | 6,391,329 | B1 | 5/2002 | Ito et al. |
| 4,640,266 | A | 2/1987 | Levy | D458,395 | S | 6/2002 | Piepgras et al. |
| 4,647,428 | A | 3/1987 | Gyulay | 6,400,104 | B1 | 6/2002 | Ham |
| 4,647,433 | A | 3/1987 | Spector | 6,402,347 | B1 | 6/2002 | Maas et al. |
| 4,714,984 | A | 12/1987 | Spector | 6,406,172 | B1 | 6/2002 | Harbers et al. |
| 4,754,372 | A | 6/1988 | Harrison | 6,416,180 | B1 | 7/2002 | Strobl |
| 4,849,181 | A | 7/1989 | Kelley et al. | D463,610 | S | 9/2002 | Piepgras et al. |
| 4,849,606 | A | 7/1989 | Martens, III et al. | 6,459,919 | B1 | 10/2002 | Lys et al. |
| 4,875,144 | A | 10/1989 | Wainwright | 6,472,876 | B1 | 10/2002 | Notohamiprodjo et al. |
| 4,885,663 | A | 12/1989 | Parker | 6,478,440 | B1 | 11/2002 | Jaworski et al. |
| 4,933,815 | A | 6/1990 | Parthasarathy | 6,478,453 | B2 | 11/2002 | Lammers et al. |
| 4,955,975 | A | 9/1990 | Mori | 6,480,649 | B2 | 11/2002 | Lee |
| 4,965,490 | A | 10/1990 | Ratner | D468,035 | S | 12/2002 | Blanc et al. |
| 4,965,701 | A | 10/1990 | Voland | 6,488,393 | B1 | 12/2002 | Burnham |
| 4,972,305 | A | 11/1990 | Blackburn | 6,499,860 | B2 | 12/2002 | Begemann |
| 4,974,136 | A | 11/1990 | Noori-Shad et al. | 6,513,954 | B2 | 2/2003 | Ebersole |
| 5,021,928 | A | 6/1991 | Daniel | 6,528,954 | B1 | 3/2003 | Lys et al. |
| 5,046,837 | A | 9/1991 | Stroomer et al. | 6,536,910 | B2 | 3/2003 | Lin |
| 5,066,085 | A | 11/1991 | Gimbutas et al. | 6,536,914 | B2 | 3/2003 | Hoelen et al. |
| 5,069,877 | A | 12/1991 | Pozzo | 6,539,656 | B2 | 4/2003 | Maas et al. |
| 5,178,839 | A | 1/1993 | Spector | 6,543,925 | B2 | 4/2003 | Kuykendal et al. |
| 5,183,323 | A | 2/1993 | Daniel | 6,547,416 | B2 | 4/2003 | Pashley et al. |
| 5,217,696 | A | 6/1993 | Wolverton et al. | 6,547,423 | B2 | 4/2003 | Marshall et al. |
| 5,247,491 | A | 9/1993 | Kwiatkowski | 6,548,967 | B1 | 4/2003 | Dowling et al. |
| 5,249,105 | A | 9/1993 | Koizumi | 6,558,022 | B2 | 5/2003 | Kawahara |
| 5,251,116 | A | 10/1993 | Wijbenga et al. | 6,573,536 | B1 | 6/2003 | Dry |
| 5,301,090 | A | 4/1994 | Hed | 6,577,080 | B2 | 6/2003 | Lys et al. |
| 5,402,517 | A | 3/1995 | Gillett et al. | 6,586,882 | B1 | 7/2003 | Harbers |
| 5,426,474 | A | 6/1995 | Rubtsov et al. | 6,601,982 | B1 | 8/2003 | Begemann et al. |
| 5,432,876 | A | 7/1995 | Appeldorn et al. | 6,608,453 | B2 | 8/2003 | Morgan et al. |
| D363,537 | S | 10/1995 | Moody | 6,613,288 | B2 | 9/2003 | Gupte |
| 5,455,750 | A | 10/1995 | Davis et al. | 6,624,597 | B2 | 9/2003 | Dowling et al. |
| 5,547,616 | A | 8/1996 | Dancs et al. | 6,626,554 | B2 | 9/2003 | Rincover et al. |
| 5,556,191 | A | 9/1996 | Maassen | 6,627,857 | B1 | 9/2003 | Tanner et al. |
| 5,561,346 | A | 10/1996 | Byrne | 6,628,885 | B1 | 9/2003 | Wilkie et al. |
| 5,568,964 | A | 10/1996 | Parker et al. | 6,629,772 | B2 | 10/2003 | Brunfeld |
| 5,647,052 | A | 7/1997 | Patel et al. | 6,642,669 | B1 | 11/2003 | MacAdam et al. |
| 5,651,942 | A | 7/1997 | Christensen | 6,648,486 | B2 | 11/2003 | Harbers et al. |
| 5,688,042 | A | 11/1997 | Madadi et al. | 6,648,496 | B1 | 11/2003 | Elghoroury et al. |
| 5,691,886 | A | 11/1997 | Stacy | 6,655,824 | B2 | 12/2003 | Tufte |
| 5,703,440 | A | 12/1997 | Kachmarik et al. | 6,672,734 | B2 | 1/2004 | Lammers |
| 5,711,591 | A | 1/1998 | Jordan | 6,676,282 | B2 | 1/2004 | Begemann et al. |
| 5,801,484 | A | 9/1998 | Bankuti et al. | 6,688,753 | B2 | 2/2004 | Calon et al. |
| 5,823,652 | A | 10/1998 | Vann | 6,712,494 | B2 | 3/2004 | Hodge |
| 5,908,231 | A | 6/1999 | Huff | 6,717,376 | B2 | 4/2004 | Lys et al. |
| 6,016,038 | A | 1/2000 | Mueller et al. | 6,720,745 | B2 | 4/2004 | Lys et al. |
| 6,099,137 | A | 8/2000 | McCormack et al. | 6,726,341 | B2 | 4/2004 | Pashley et al. |
| 6,106,786 | A | 8/2000 | Akahoshi | 6,733,161 | B2 | 5/2004 | Tufte |
| 6,120,737 | A | 9/2000 | Zembrodt | D491,678 | S | 6/2004 | Piepgras et al. |
| 6,143,313 | A | 11/2000 | Ito et al. | D492,042 | S | 6/2004 | Piepgras et al. |
| 6,150,774 | A | 11/2000 | Mueller et al. | 6,742,914 | B2 | 6/2004 | Prodell |
| 6,166,496 | A | 12/2000 | Lys et al. | 6,745,506 | B2 | 6/2004 | Maas et al. |
| 6,200,002 | B1 | 3/2001 | Marshall et al. | 6,758,573 | B1 | 7/2004 | Thomas et al. |
| 6,211,626 | B1 | 4/2001 | Lys et al. | 6,774,584 | B2 | 8/2004 | Lys et al. |
| 6,217,188 | B1 | 4/2001 | Wainwright et al. | 6,777,891 | B2 | 8/2004 | Lys et al. |
| 6,220,722 | B1 | 4/2001 | Begemann | 6,779,905 | B1 | 8/2004 | Mazursky et al. |
| 6,220,742 | B1 | 4/2001 | Lloyd et al. | 6,781,329 | B2 | 8/2004 | Mueller et al. |
| 6,234,645 | B1 | 5/2001 | Borner et al. | 6,788,011 | B2 | 9/2004 | Mueller et al. |
| 6,234,648 | B1 | 5/2001 | Borner et al. | 6,793,360 | B2 | 9/2004 | Goslee |
| 6,234,649 | B1 | 5/2001 | Katougi | 6,796,685 | B1 | 9/2004 | Nemirow |
| 6,254,248 | B1 | 7/2001 | McAuley et al. | 6,801,003 | B2 | 10/2004 | Schanberger et al. |
| 6,270,720 | B1 | 8/2001 | Mandish | 6,802,635 | B2 | 10/2004 | Robertson et al. |
| 6,292,901 | B1 | 9/2001 | Lys et al. | 6,806,659 | B1 | 10/2004 | Mueller et al. |
| 6,294,800 | B1 | 9/2001 | Duggal et al. | 6,815,724 | B2 | 11/2004 | Dry |
| 6,299,338 | B1 | 10/2001 | Levinson et al. | 6,817,731 | B2 | 11/2004 | Tufte |
| 6,318,876 | B1 | 11/2001 | Sigro et al. | 6,831,303 | B2 | 12/2004 | Dry |
| 6,339,298 | B1 | 1/2002 | Chen | 6,833,539 | B1 | 12/2004 | Maeda |
| 6,340,868 | B1 | 1/2002 | Lys et al. | 6,837,591 | B2 | 1/2005 | Tufte |
| 6,371,450 | B1 | 4/2002 | Davis et al. | 6,840,646 | B2 | 1/2005 | Cornelissen et al. |
| 6,371,634 | B1 | 4/2002 | Tufte | 6,848,822 | B2 | 2/2005 | Ballen et al. |
| D457,667 | S | 5/2002 | Piepgras et al. | 6,851,844 | B2 | 2/2005 | Guy |
| D457,669 | S | 5/2002 | Piepgras et al. | 6,854,208 | B1 | 2/2005 | Chuang et al. |
| D457,974 | S | 5/2002 | Piepgras et al. | 6,854,854 | B2 | 2/2005 | Hoelen et al. |

| | | |
|---|---|---|
| 6,854,869 B1 | 2/2005 | Fernandez |
| D503,467 S | 3/2005 | Flashinski et al. |
| 6,869,202 B2 | 3/2005 | Tufte |
| 6,869,204 B2 | 3/2005 | Morgan et al. |
| 6,874,909 B2 | 4/2005 | Vanderschuit |
| 6,880,948 B2 | 4/2005 | Koch et al. |
| 6,883,929 B2 | 4/2005 | Dowling |
| 6,883,931 B2 | 4/2005 | Tufte |
| 6,888,322 B2 | 5/2005 | Dowling et al. |
| 6,890,085 B2 | 5/2005 | Hacker |
| 6,897,624 B2 | 5/2005 | Lys et al. |
| 6,902,301 B2 | 6/2005 | Kieronski |
| 6,921,184 B2 | 7/2005 | Tufte |
| 6,936,978 B2 | 8/2005 | Morgan et al. |
| 6,951,401 B2 | 10/2005 | Van Hees et al. |
| 6,952,079 B2 | 10/2005 | Shiang et al. |
| 9,957,897 | 10/2005 | Nelson et al. |
| 6,965,205 B2 | 11/2005 | Piepgras et al. |
| 6,966,665 B2 | 11/2005 | Limburg et al. |
| 6,976,774 B2 | 12/2005 | Reiss |
| 7,008,096 B1 | 3/2006 | Coushaine et al. |
| 7,038,399 B2 | 5/2006 | Lys et al. |
| 7,046,920 B2 | 5/2006 | Flashinski |
| 7,052,152 B2 | 5/2006 | Harbers et al. |
| 7,067,981 B2 | 6/2006 | Nishio et al. |
| 7,075,224 B2 | 7/2006 | Coushaine |
| 7,080,932 B2 | 7/2006 | Keuper |
| 7,086,756 B2 | 8/2006 | Maxik |
| 7,086,767 B2 | 8/2006 | Sidwell et al. |
| 7,093,958 B2 | 8/2006 | Coushaine |
| 7,104,679 B2 | 9/2006 | Shin et al. |
| 7,109,665 B2 | 9/2006 | Green |
| 7,116,294 B2 | 10/2006 | Stopa |
| 7,160,012 B2 | 1/2007 | Hilscher et al. |
| 7,175,302 B2 | 2/2007 | Kazar et al. |
| 2001/0014019 A1 | 8/2001 | Begemann |
| 2001/0035853 A1 | 11/2001 | Hoelen et al. |
| 2001/0038532 A1 | 11/2001 | Harbers et al. |
| 2001/0049893 A1 | 12/2001 | Maas et al. |
| 2002/0006044 A1 | 1/2002 | Harbers et al. |
| 2002/0030997 A1 | 3/2002 | Tufte |
| 2002/0071285 A1 | 6/2002 | Tufte |
| 2002/0075671 A1 | 6/2002 | Tufte |
| 2002/0075674 A1 | 6/2002 | Tufte |
| 2002/0105800 A1 | 8/2002 | Tufte |
| 2002/0118538 A1 | 8/2002 | Calon et al. |
| 2002/0131273 A1 | 9/2002 | Tufte |
| 2002/0135997 A1 | 9/2002 | Lammers |
| 2002/0136017 A1 | 9/2002 | Tufle |
| 2002/0141058 A1 | 10/2002 | Itoh |
| 2003/0007887 A1 | 1/2003 | Roumpos et al. |
| 2003/0021117 A1 | 1/2003 | Chan |
| 2003/0039115 A1 | 2/2003 | Lin |
| 2003/0046842 A1 | 3/2003 | Maas et al. |
| 2003/0071932 A1 | 4/2003 | Tanigaki |
| 2003/0076677 A1* | 4/2003 | Mohacsi et al. ............. 362/226 |
| 2003/0078791 A1 | 4/2003 | Tufte |
| 2003/0095409 A1 | 5/2003 | Cheng |
| 2003/0137258 A1* | 7/2003 | Piepgras et al. ............. 315/291 |
| 2003/0209183 A1 | 11/2003 | Tufte |
| 2003/0231488 A1 | 12/2003 | Albee |
| 2004/0066652 A1 | 4/2004 | Hong |
| 2004/0070967 A1 | 4/2004 | Kennedy |
| 2004/0095078 A1 | 5/2004 | Leong |
| 2004/0095754 A1 | 5/2004 | Hsu |
| 2004/0095780 A1 | 5/2004 | Reed |
| 2004/0109317 A1 | 6/2004 | Ribarich |
| 2004/0124790 A1 | 7/2004 | Han et al. |
| 2004/0179358 A1 | 9/2004 | Tufle |
| 2004/0189218 A1 | 9/2004 | Leong et al. |
| 2004/0232825 A1 | 11/2004 | Sorg |
| 2004/0246711 A1 | 12/2004 | Brenchley et al. |
| 2004/0257798 A1 | 12/2004 | Hart et al. |
| 2004/0264185 A1 | 12/2004 | Grotsch et al. |
| 2004/0264187 A1* | 12/2004 | Vanderschuit ............... 362/235 |
| 2005/0024892 A1 | 2/2005 | Cabrera |
| 2005/0030747 A1 | 2/2005 | Bogdal |
| 2005/0036300 A1 | 2/2005 | Dowling et al. |
| 2005/0047127 A1 | 3/2005 | Tutman |
| 2005/0074358 A1 | 4/2005 | Hart et al. |
| 2005/0099108 A1 | 5/2005 | Hofmann et al. |
| 2005/0104503 A1 | 5/2005 | Ellens et al. |
| 2005/0128751 A1 | 6/2005 | Roberge et al. |
| 2005/0162101 A1 | 7/2005 | Leong et al. |
| 2005/0169015 A1 | 8/2005 | Luk et al. |
| 2005/0169643 A1 | 8/2005 | Franklin |
| 2005/0169666 A1 | 8/2005 | Porchia et al. |
| 2005/0169812 A1 | 8/2005 | Helf et al. |
| 2005/0173675 A1 | 8/2005 | Schmidt et al. |
| 2005/0174473 A1 | 8/2005 | Morgan et al. |
| 2005/0185392 A1 | 8/2005 | Walter et al. |
| 2005/0185398 A1 | 8/2005 | Scannell, Jr. |
| 2005/0195598 A1 | 9/2005 | Dancs et al. |
| 2005/0195600 A1 | 9/2005 | Porchia et al. |
| 2005/0207152 A1 | 9/2005 | Maxik |
| 2005/0213342 A1 | 9/2005 | Tufte |
| 2005/0258439 A1 | 11/2005 | Dry |
| 2005/0258440 A1 | 11/2005 | Dry |
| 2005/0259416 A1 | 11/2005 | Gauna et al. |
| 2005/0265018 A1 | 12/2005 | Yasuda et al. |
| 2005/0265023 A1 | 12/2005 | Scholl |
| 2005/0269581 A1 | 12/2005 | Dry |
| 2005/0275626 A1 | 12/2005 | Mueller et al. |
| 2005/0281030 A1 | 12/2005 | Leong et al. |
| 2005/0285538 A1 | 12/2005 | Jaworski et al. |
| 2006/0001677 A1 | 1/2006 | Webb et al. |
| 2006/0002102 A1 | 1/2006 | Leonard |
| 2006/0002110 A1 | 1/2006 | Dowling et al. |
| 2006/0006784 A1 | 1/2006 | Takahara et al. |
| 2006/0022214 A1 | 2/2006 | Morgan et al. |
| 2006/0023447 A1 | 2/2006 | Justel et al. |
| 2006/0045818 A1 | 3/2006 | Moreland |
| 2006/0055315 A1 | 3/2006 | Bokor et al. |
| 2006/0071589 A1 | 4/2006 | Radkov |
| 2006/0081871 A1 | 4/2006 | Streubel |
| 2006/0082333 A1 | 4/2006 | Laski |
| 2006/0083013 A1 | 4/2006 | Wanninger et al. |
| 2006/0103291 A1 | 5/2006 | Ellens et al. |
| 2006/0114670 A1 | 6/2006 | Ho |
| 2006/0120080 A1 | 6/2006 | Sipinski et al. |
| 2006/0176690 A1 | 8/2006 | Yuen |
| 2006/0220990 A1 | 10/2006 | Coushaine et al. |
| 2006/0226795 A1 | 10/2006 | Walter et al. |
| 2006/0238136 A1 | 10/2006 | Johnson, III et al. |
| 2006/0244000 A1 | 11/2006 | Jager et al. |
| 2006/0248783 A1 | 11/2006 | Lindquist et al. |
| 2006/0275040 A1 | 12/2006 | Franklin |
| 2007/0086199 A1 | 4/2007 | Demarest et al. |

FOREIGN PATENT DOCUMENTS

| | | |
|---|---|---|
| WO | WO 01/78488 A2 | 10/2001 |
| WO | WO 2004/068945 A1 | 8/2004 |
| WO | WO 2004/073399 A1 | 9/2004 |
| WO | WO 2005/086245 | 9/2005 |
| WO | WO 2008/002427 | 1/2008 |

OTHER PUBLICATIONS

International Searching Authority, "International Search Report and Written Opinion", Feb. 28, 2008, 10 Pages.

* cited by examiner

*Primary Examiner*—Ali Alavi
*Assistant Examiner*—Evan Dzierzynski
(74) *Attorney, Agent, or Firm*—Miller, Matthias & Hull

(57) ABSTRACT

A replacement device for a light bulb includes a translucent shell and a base. The base supports a plurality of colored lights positioned so as to emit a light show through the shell. The base is configured to be received in a conventional light socket. The base also includes a compartment for receiving and securing a replaceable volatile active cartridge for enabling the device to emit an active ingredient from the cartridge when the cartridge is secured in the compartment. A dimmable white light source may also provided in the shell as a source of illumination. Thus, a single device is used as a replacement for a conventional light bulb and is a combination white light source/colored light show source/volatile active source.

19 Claims, 24 Drawing Sheets

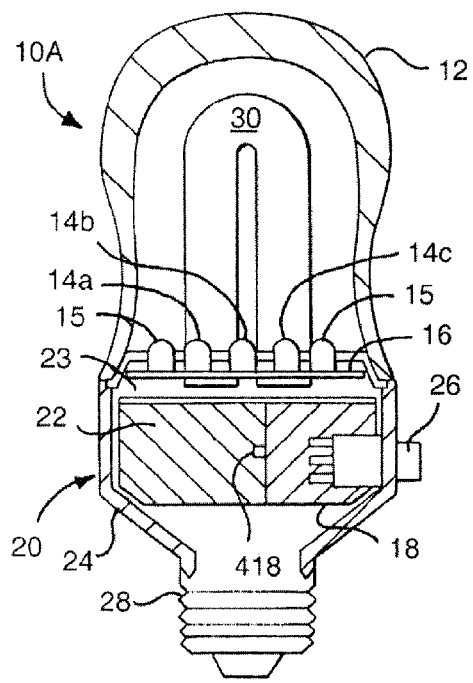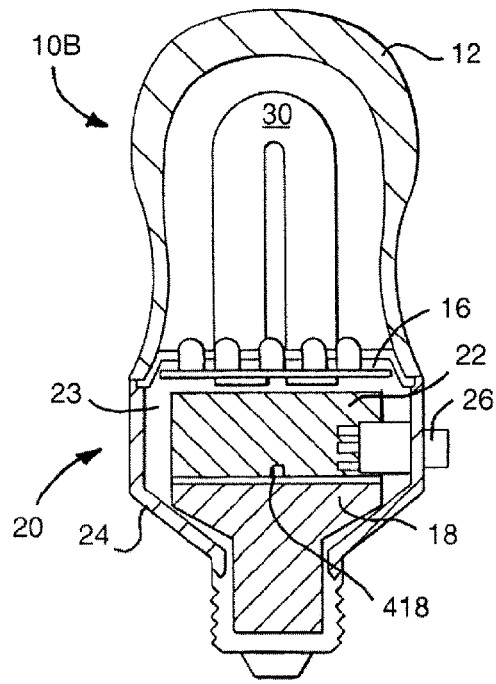
FIG. 1A  FIG. 1B
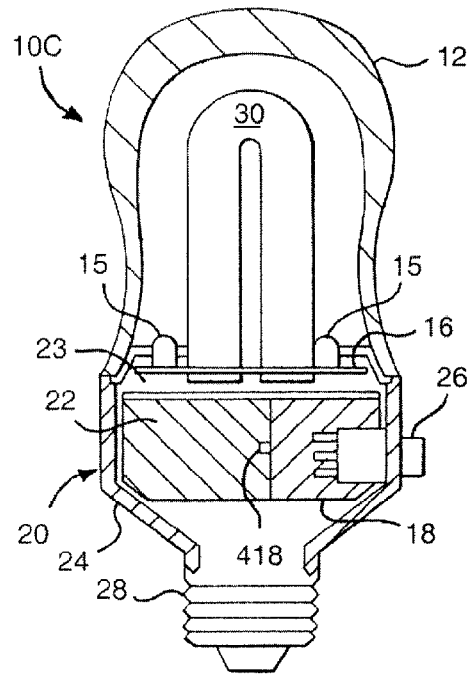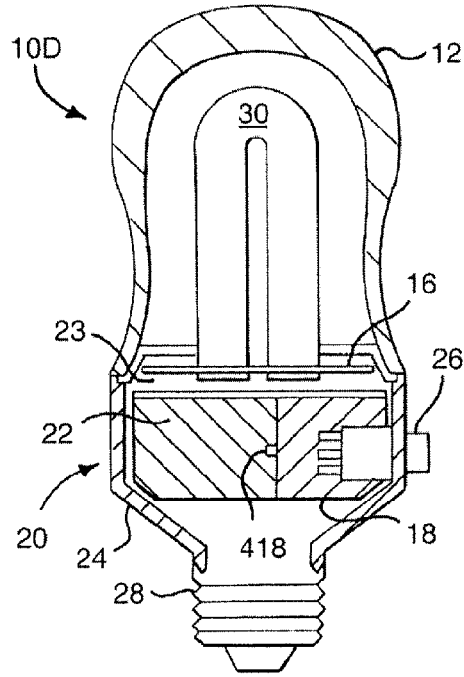
FIG. 1C  FIG. 1D

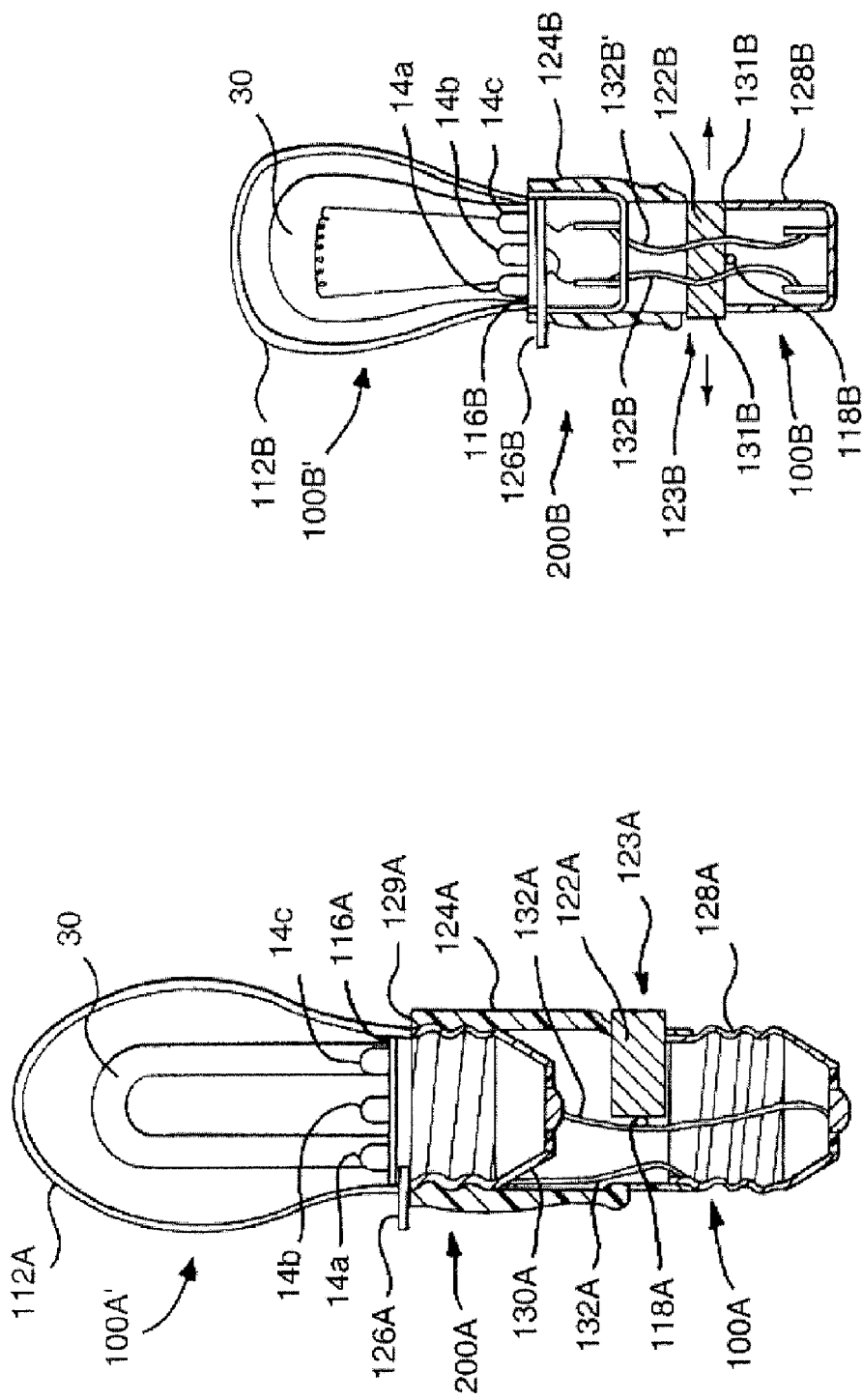

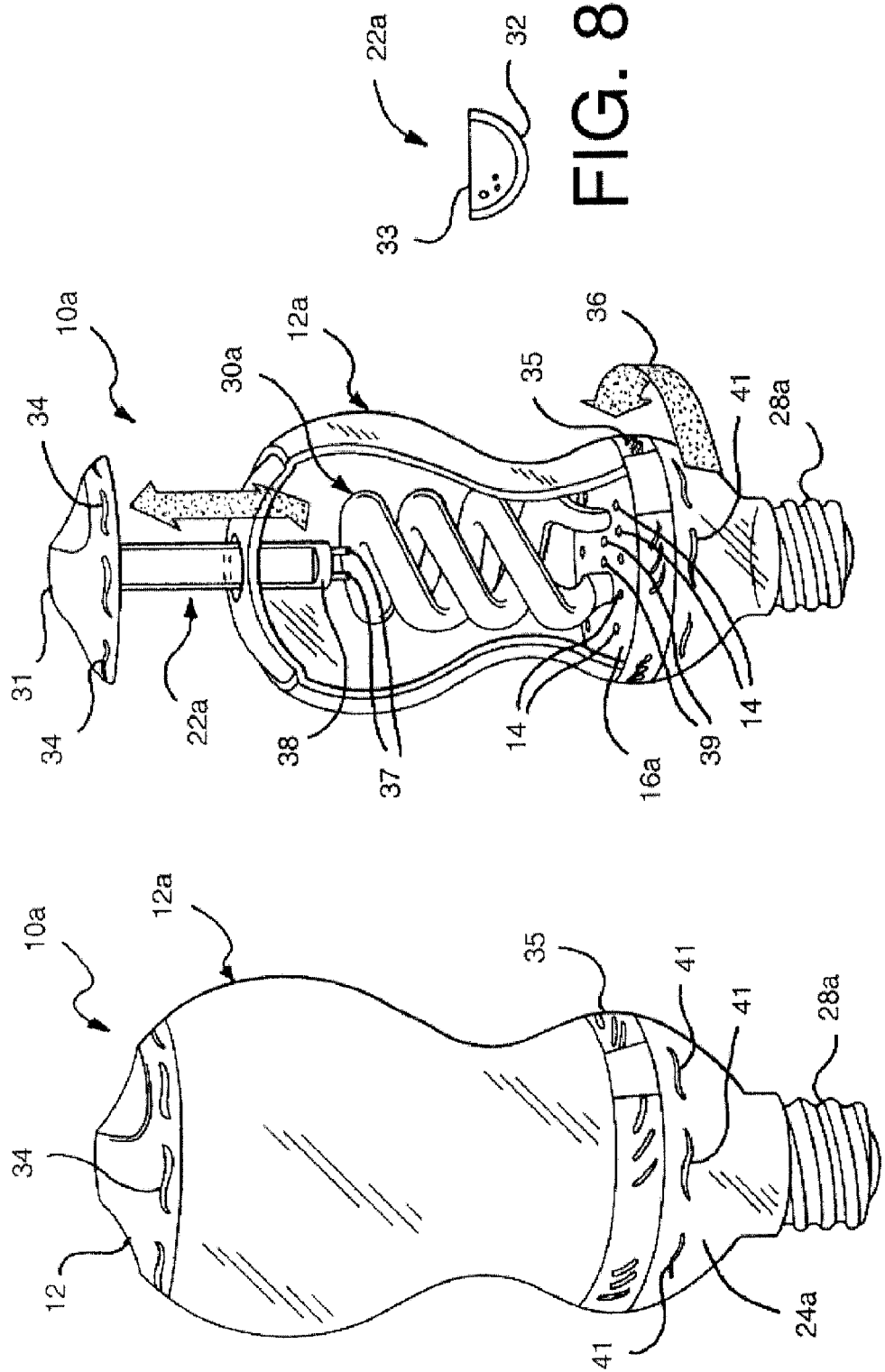

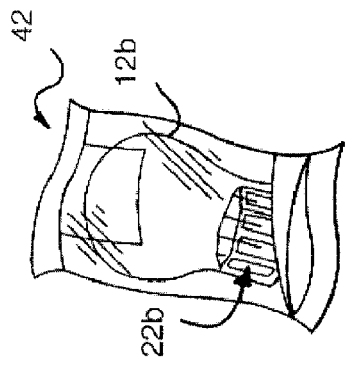
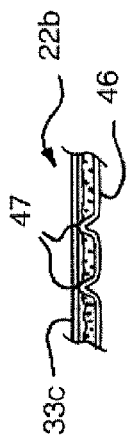
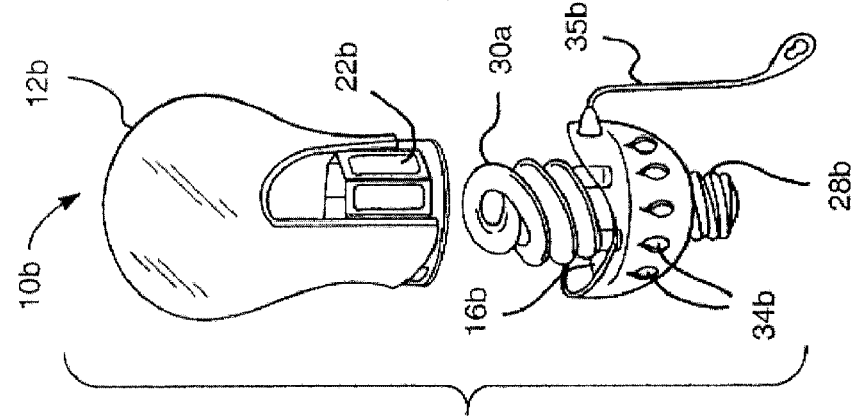
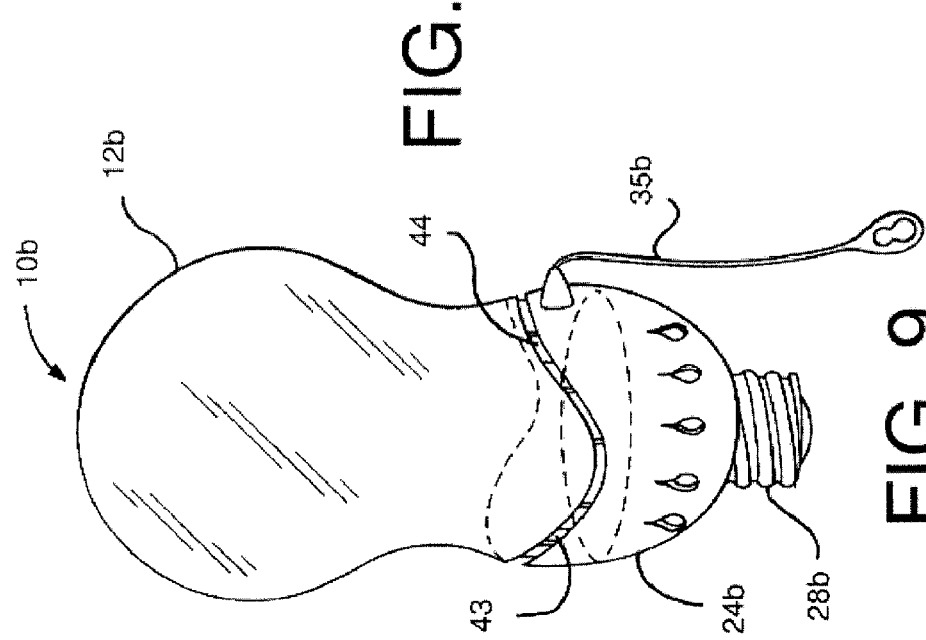

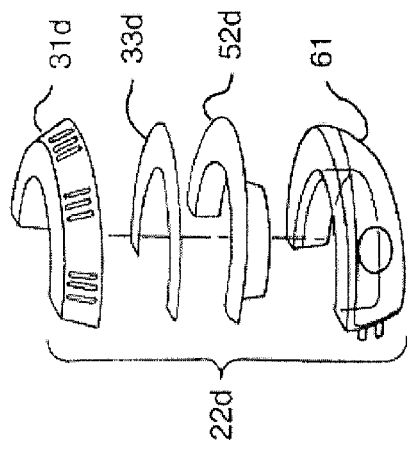
FIG. 19
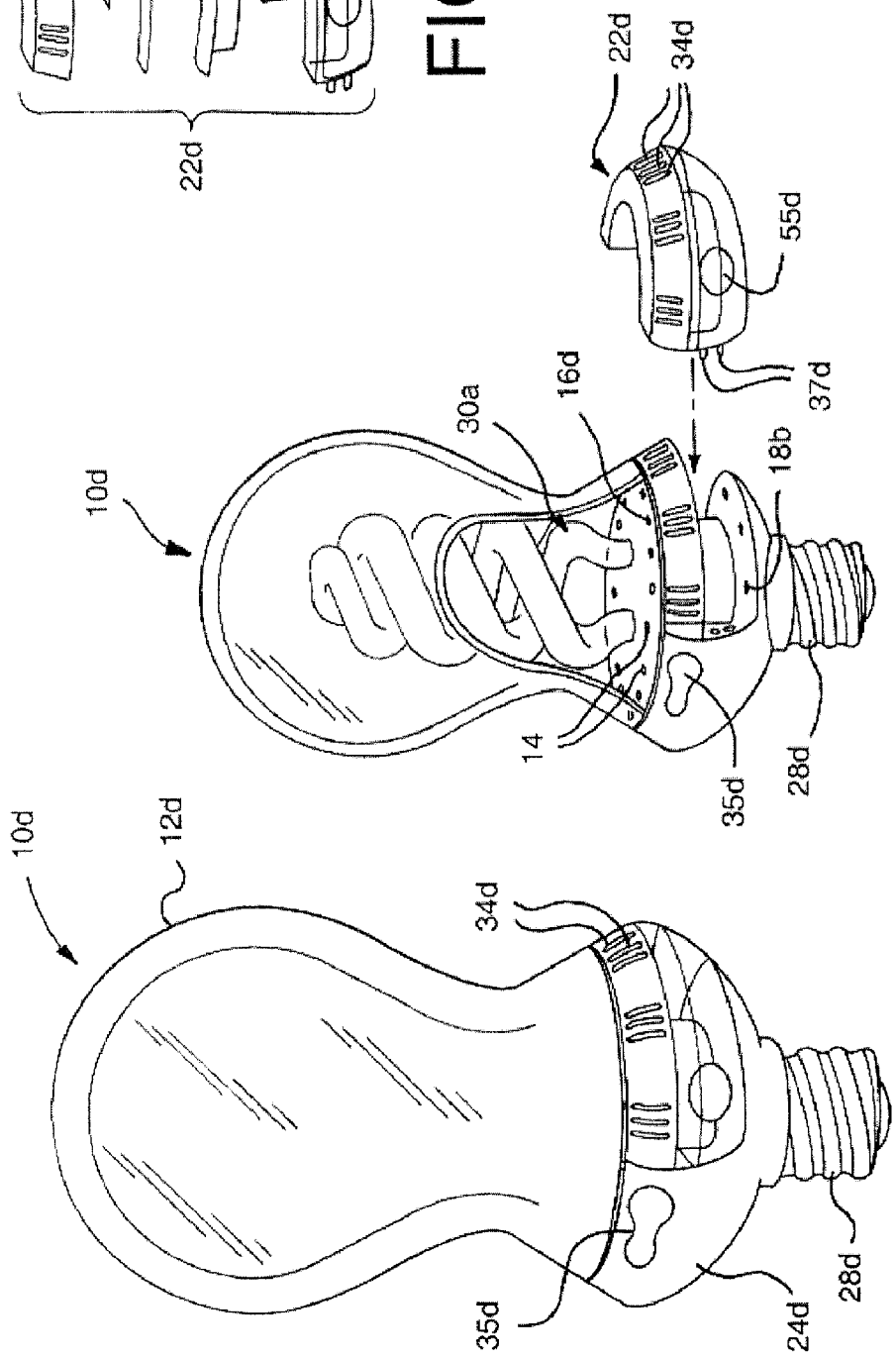
FIG. 18
FIG. 17

COMBINATION WHITE LIGHT AND COLORED LED LIGHT DEVICE WITH ACTIVE INGREDIENT EMISSION

CROSS-REFERENCE TO RELATED APPLICATIONS

This application is a continuation-in-part of U.S. patent application Ser. No. 11/426,055, filed on Jun. 23, 2006 now U.S. Pat. No. 7,318,659 which is a continuation-in-part of U.S. patent application Ser. No. 11/069,964, filed on Mar. 3, 2005, now U.S. Pat. No. 7,246,919 which claims priority to Provisional Patent Application Ser. No. 60/549,154, filed on Mar. 3, 2004. This application is also a continuation-in-part of U.S. patent application Ser. No. 10/561,822, filed on Apr. 25, 2006, still pending, which claims priority to Provisional Patent Application Ser. No. 60/483,913 filed on Jul. 2, 2003.

BACKGROUND

1. Technical Field

A substitute for a conventional light bulb is disclosed which provides various combinations of features including, but not limited to, the emission of white light, colored light in the form of changing colored light shows and active ingredient vapor emission. The disclosed device screws into a conventional light socket and the active ingredient is dispensed from replaceable cartridges or bottles. The device may also serve as an adapter for receiving a conventional light bulb. The specific active ingredient emitted may be coordinated with the specific light show performed. A plurality of light shows may be programmed into the memory of the device and memory chips containing new light shows may be provided or the active ingredient cartridges may be equipped with a chip containing one or more light shows that are designed with the active ingredient in mind. The colored light may be produced by RGB LED clusters or filtered white light sources using conventional colored lenses, shrouds or covers or an LCD filter.

2. Description of the Related Art

Creating a pleasant ambience is a popular aspect of home decor. This is often achieved through various combinations of pleasant fragrances and mood lighting. Lighting can also be combined with other functions such as air sanitization, air deodorization, and the controlled release of insect repellent, insect attractant and insecticide. Conventional products such as scented candles, mood lighting devices, fragrance dispensers, and the like, are commonly used to create a pleasant environment in the home. While those conventional products help to create a pleasant living environment and ambiance, they have their drawbacks.

For example, while scented candles create soft light and fragrance, which creates a pleasant mood, candles are a potential fire hazard and often produce unwanted smoke and wax drippings. Traditional light fixtures and lamps do not provide the color effects, fragrance emission or other active emission that users often desire. While stand-alone aesthetic devices are available for providing lighting effects (such as color changing and the like), these standalone devices take up space around the home and add to the clutter that many consumers are trying to avoid. Also, because such stand-alone devices are typically placed in highly visible locations, they need to be aesthetically designed to suit the personal tastes of different categories of buyers, requiring additional design costs.

Conventional fragrance dispensers, such as plug-in diffusers, can provide pleasing aromas in a relatively inexpensive, compact package. However, such conventional fragrance dispensers generally take up outlets and are often located out of sight, causing a user to forget to adjust or refill the device. While these fragrance dispensers may also provide light, because the devices are used in existing electrical outlets, they are generally positioned too low to provide effective lighting features, other than to operate as a nightlight.

Conventional nightlights include only white light emission in combination with fragrance emission. While a single scent may be provided in the form of a decorative diffuser, colored nightlights are not generally available and there is no coordination between the light color emitted and the particular fragrance emitted. Further, sophisticated multi-colored lights that change color and that are aesthetically pleasing in combination with fragrance emission are not currently available.

Further, numerous needs exist for the combination of white light and/or colored light with other volatile active emission other than fragrances such as air sanitization, air deodorization, the controlled release of insect repellent insect attractant, insecticide, aromatherapy volatiles or other non-flagrant materials (any of which may be combined with flagrant materials if necessary to make the ambient environment more tolerable).

Therefore, multiple needs exist for devices that combine one or more of the following functions: white light emission; colored light emission; colored light shows; fragrance emission; air sanitization; air deodorization; insecticide emission; insect repellent emission; aromatherapy material emission; light emission that repels insects; light emission that attracts insects; and any combinations thereof.

SUMMARY OF THE DISCLOSURE

In view of the drawbacks of the lighting and fragrance devices currently on the market, devices are disclosed herein which provide various combinations of lighting and emission of volatile actives.

In a refinement, the device intended primarily for use indoors combines one or more of the following: white light emission with optional white light intensity adjustment of dimming; colored light shows; and fragrance and/or volatile active emission without adding clutter to a room, without requiring the purchase of new fixtures, without taking up additional electrical outlets, without requiring aesthetically pleasing designs for the unit itself, and without presenting the fire hazards associated with open flames.

In such a refinement, a substitute for a conventional light bulb that can be used indoors or outdoors is disclosed that is configured to mate with a conventional ("Edison") light socket, that can provide various combinations of functions such as white light, aesthetically pleasing colored lighting effects, fragrance emission and/or some sort of volatile active ingredient emission (e.g., insect repellent insecticide, air sanitizer, air deodorizer, etc.).

In one aspect, a disclosed device includes a translucent housing that may comprise a translucent outer shell coupled to a base configured to be received in a conventional light socket, at least one RGB LED cluster positioned within the housing so as to emit light through the housing, and a replaceable active ingredient cartridge or bottle that may be received in a compartment disposed on the base of the device or that may be a part of the translucent outer shell.

In a refinement, a white light source is provided in addition to the RGB LED cluster.

In a different refinement, a white light source is provided in stead of the RGB LED cluster.

In another aspect, a disclosed device includes a base configured to mate with a light socket for receiving the light bulb, a translucent shell coupled to the base, and at least one RGB LED cluster coupled to the base and beneath the outer shell. An active ingredient dispenser is supported by the base and dispenses an active ingredient from device when the active ingredient is provided therein. A control mechanism is provided, by which the device can be controlled by a user to change at least one of the color of the light or light show emitted from the housing by LEDs, and an output rate of the active ingredient.

In a refinement a white light source is provided. In a related refinement, the white light source is a fluorescent lamp in the circuitry of the device includes a dimming capability for the fluorescent lamp. In a related refinement, the white light source is a low voltage clamp such as a low voltage halogen lamp or other low voltage incandescent lamp. The white light source can also be a white LED. In any refinement, intensity adjustment or dimming of the white light source as well as the colored light effects or colored light shows can be provided.

In another refinement, the colored light show is carried out by a RGB incandescent lamp cluster such as a RGB low voltage incandescent lamp cluster, linked to an appropriate circuitry for carrying out one or more light shows.

As noted above, the disclosed device may provide white light typically associated with a conventional light bulb, as well as colored options, color-changing effects, and/or active emission such as fragrance emission. In addition, all of these options may be provided in one device that can be used as a replacement bulb that can be placed in existing lamps already found in the user's home. Heat for enhancing the active emission can be supplied by the white light source, colored light source or a resistance heater built into the device and controlled by the circuitry of the device.

In a refinement, colored light sources are not disposed within the outer shell and only a white light source is provided. However, the outer shell is constructed of one or more LCD filters that strategically block colors of light while allowing other colors of light to pass their through. As a result, the LCD filters are used to carry out the colored light shows and therefore are linked directly to the electronic circuitry of the device. A plurality of flat LCD filters may be employed, however curved LCD filters are available.

In another aspect, two devices adapted to be received in a common light socket ale connected together in series. Specifically, a first device includes a male base that is received within a light socket. The body of the first device houses one or more functional elements such as an active dispenser, colored lights for a colored light show or a white light element and terminates at a female receptacle for receiving a male base of a second device. The second device is received in the female receptacle of the first device and typically includes one or more additional functional elements not found in the first device such as a white light source, colored light source or active ingredient dispenser. Thus, using this "piggy-back" scheme, functional elements can be added by using a second device.

In a refinement, the volatile active ingredient controls, attracts, repels and/or terminates insects. The insect control functions may be combined with fragrance emission, a deodorizing function or an air sanitization function.

Thus, in a refinement, the volatile active may provide a function selected from the group consisting of: insect control, insect termination, insect attraction, insect repellency, moth termination, fragrance emission, or deodorization, air sanitization, aromatherapy, volatile medicine emission and any combination thereof.

In a related refinement, a device made in accordance with this disclosure can release an active that repels insects, such as mosquitoes, to either keep such insects out of a home or to keep such insects away from an outdoor area such as a patio or porch. The active can repel or kill the problematic insects. In the alternative, the disclosed devices may be used to attract insects and keep them away from an outdoor area such as a porch or deck. Indoor applications include the use of a disclosed device in a closet that emits a volatile active that kills moths and further that emits white light or, optionally, colored light. The disclosed devices may also be used to emit insect repellent or insecticides indoors in certain jurisdictions and therefore these functions can be combined with the emission of white light and/or colored light shows.

Thus, the combination white light/colored light show/active emitter device disclosed herein can be used in porch/deck lighting systems and outdoor perimeter lighting systems.

In another refinement, combination white light/colored light show/active emitter device can be used in an enclosed area such as a closet and the volatile active can be an insecticide directed at moths, roaches, houseflies, frit flies, gnats and/or ants.

In a refinement, the LEDs may be used to provide an additional or an alternative source of white light.

In a refinement, light sources, either white or colored, may be used as heat sources for active ingredient emission.

In another refinement, the fragrance or active delivery may be provided by scented oil or scented gels provided in cartridges which may be replaceably secured in/to the device, to provide the desired fragrance emission. This allows a user to change between different fragrances and/or replace empty cartridges, without the need to change the entire bulb device. In addition, the device can be programmable so that a user may change the lighting options (i.e., change the brightness or color, activate a color show or change color shows), and/or the fragrance emission rate.

In another refinement, the refill cartridge or bottle includes a memory chip programmed with one or more light shows and in a further refinement of this concept, the light shows are coordinated with the active contained in the refill cartridge. In short, either the fragrance emitted or another type of active, such as insect repellant, can be coordinated with the one or more light show exhibited by the device.

In another refinement, the outer shell or globe of the device may itself include the active ingredient or fragrance dispense. In such a refinement, the outer shell includes an inner and outer wall with avoids base therebetween that can accommodate an active material or fragrance. Thus, the outer shell is the active or fragrance dispenser. In another refinement of this concept, the outer shell is connected to active ingredient or volatile active cartridges and is sold with the replacement cartridges.

In another refinement, a refill cue may be provided by the circuitry of the device that informs the user when the active or fragrance has become depleted and when a refill cartridge or bottle is needed.

In another refinement, a remote control device may be provided enabling the user to change light shows, stop a light show and turn the fluorescent lamp on or off. The remote control device may also be provided with a fragrance or active dispenser.

In another refinement, one or more control buttons may be provided on the outside of the base or housing which enables the user to change light shows, stop or pause a light show, turn the fluorescent lamp on or off, or turn the device on or off.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 1A is a cross-sectional view of a disclosed combination white light/colored light show/active vapor emission device with a threaded, screw-in base.

FIG. 1B is a cross-sectional view of another device with a threaded, screw-in base.

FIG. 1C is a cross-sectional view of a white light/active vapor emission device with a threaded, screw-in base.

FIG. 1D is a cross-sectional view of another white light/active vapor emission device with a threaded, screw-in base.

FIG. 2A is a cross-sectional view of a first device or adapter with a threaded screw-in base and equipped with an active vapor emission dispenser wherein the first device is coupled to a second threaded screw-in device equipped with white light/colored light show capability.

FIG. 2B is a cross-sectional view of a first device or adapter with a plug-in base and equipped with an active vapor emission dispenser wherein the first device is coupled to a second plug-in device equipped with white light/colored light show capability.

FIG. 6 is an elevational view of yet another combination white light/colored light show/active ingredients emission device made in accordance with this disclosure.

FIG. 7 is a sectional and partially exploded view of the device shown in FIG. 6.

FIG. 8 is a top sectional view of the active ingredient cartridge shown in FIG. 7.

FIG. 9 is an elevational view of yet another combination white light/colored light show/active ingredient emission device made in accordance with this disclosure, particularly illustrating a lanyard on/off switch.

FIG. 10 is a sectional and partially exploded view of the device shown in FIG. 9, particularly illustrating the use of a series of volatile active cartridges arranged cylindrically within the outer cover and on top of the base.

FIG. 11 is a partial sectional view of the active ingredient cartridges shown in FIG. 10.

FIG. 12 is an elevational view of a replacement outer shell and active ingredient cartridges for the device shown in FIGS. 9 and 10.

FIG. 13 is an illustration of a remote control for use with any of the combination devices disclosed herein.

FIG. 17 is an elevational view of yet another combination white light/colored light show/active ingredient emission device made in accordance with this disclosure, particularly illustrating a curved trough-type active ingredient cartridge disposed in the base of the device.

FIG. 18 is a partial sectional and exploded view of the device shown in FIG. 17, particularly illustrating the placement of the active ingredient cartridge in the base of the device.

FIG. 19 is an exploded view of the active ingredient cartridge and vented cover for the device shown in FIGS. 17 and 18.

Figure 1E:
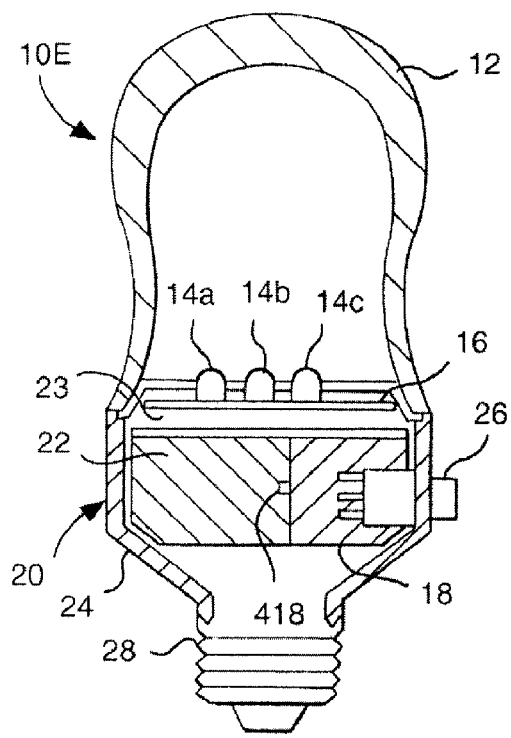
FIG. 1E is a cross-sectional view of a disclosed combination colored light show/active vapor emission device with a threaded, screw-in base.

It should be under stood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

FIGS. 1A-1G illustrate screw-in combination white light/colored light show/active ingredient emission devices 10a-10g made in accordance with this disclosure. While the disclosed devices can mate with any one of a number of lighting fixtures (such as conventional fixtures for receiving incandescent, halogen, or fluorescent bulbs), for exemplary purposes, the description provided herein refers to an Edison-style, screw-in light device that mates with a conventional incandescent light socket with a threaded female receptacle. Of course, the devices of this disclosure may be embodied in any light bulb that mates with a light socket/power source.

Device 10A of FIG. 1A includes a translucent housing or cover 12 mounted onto a base 24. The bottom of base 24 comprises a threaded male, screw-in connector 28, which is configured to mate with a threaded female socket of a conventional lamp or other lighting fixture. When connector 28 is mated with such a socket, AC power is provided to the device 10 from the lamp or lighting fixture.

The power is provided to an LED board (light array) 16, on which LEDs 14a (red), 14b (green), 14c (blue), and 15 (white) are mounted. In the embodiments illustrated in FIGS. 6-31, the LEDs are provided in a three diode cluster including red, green and blue diodes referred to below as a RGB LED cluster. These LEDs may be operated in any one of a number of combinations to provide a specific color of light, color shows or patterns that are pleasing to a user. For example, the LEDs may be operated as described in commonly assigned International Publication No. WO2005/003625, US Publication Nos. US 2005/0169812 and US 2005/0169666, all of which are incorporated herein by reference. The outer shell 12 may act as a light diffuser, to cause a user to perceive the intended color, rather than the activation of distinct LEDs of different colors. Alternatively, a separate diffuser may be provided inside the outer shell 12. The diffuser 12 operates to combine the lights from the different LEDs to form a single color, the perception of which is dictated by the relative intensities of the individual colored LEDs. In other embodiments, no diffuser at all may be used, in order to allow a user to simultaneously perceive multiple colors of the different LEDs. Also, when insect control is an issue, the lighting effects may be programmed to attract or repel insects, using conventionally known lighting techniques for the same. The diffuser 12 may also act is a fragrance dispenser as the walls of the diffuser 12 may absorb fragrance or other active ingredients or the diffuser 12 may include inner and outer walls with a void space therebetween that accommodates a fragrance oil. The diffuser 12 may also be coupled to replaceable volatile active cartridges and sold as a refill item as explained below in connection with FIG. 12.

Still referring to FIG. 1A, the white LEDs 15 can provide a primary source of illumination for the device 10 but the more preferable method is to employ a fluorescent lamp 30 as a white light source and, more specifically, the twisted or coiled fluorescent lamp 30a as shown in FIGS. 7, 10, 15, 18, 21 and 25 below. Alternatively (or in addition), the red, green, and blue LEDs 14a-14c may be configured to, in combination, produce white light, when their respective wavelengths are mixed by a diffuser or the like. Examples of a RGB LED cluster producing white light can be found in commonly assigned Provisional Application No. 60/641,441, which is incorporated herein by reference. See also FIG. 5B below. Other conventional light sources, such as halogen or other types of fluorescent lights may also be used as a primary light source. In the embodiment shown in FIG. 1, a compact fluorescent bulb 30 is disposed coupled to the base 24 in the housing 12, and provides the primary source of illumination. Alternatively, when the fluorescent bulb 30 is used, the white LEDs 15 may be omitted and vice versa.

Power is also preferably provided to volatile active dispenser 20, which, in this embodiment, comprises a resistance heater 18. It should be noted, however, that any one of a number of active dispensers may be used. For example, see the heating element 18a and wiring 19 for the heating element 18a of FIG. 15, the heating element 18b of FIG. 18, and the heating element 18c and wiring 19a for the heating element 18b of FIG. 25.

Heat is applied to increase the evaporation late of fragrance oil, fragrance gel, insecticide, insect repellent, insect attractant, air sanitizer, deodorizer, medicine, aromatherapy material or the like. In other embodiments, fan-assisted evaporation devices, piezo-electrically actuated atomization devices, and/or unassisted fragrance dispensers may be substituted. Unassisted volatile active dispensers may simply include venting mechanisms that expose the volatile active to the ambient environment, or other such designs that enhance/ provide convective airflow across a volatile active delivery medium. Of course, if unassisted volatile active dispensers are used, power need not be provided to the dispenser. These alternative devices are known in the art, and will not be described in detail herein.

It will be noted here that heat from the white light source and/or heat from the colored light sources may provide sufficient heat for satisfactory emission rates for many volatile actives. Mechanical fans may also be used to enhance distribution or may be used instead of heating elements.

Regarding the use of insect control actives, the disclosed devices may be particularly useful for patio/deck lighting and outdoor promoter lighting where it is desirable to keep insects away from a defined area such as a patio, deck or pool area and/or word is desirable to attract insects away from such a defined area. Still further, use of the disclosed devices in an enclosed area such as the closet provides the opportunity for the volatile active to be a moth, cockroach, housefly, fruit fly, ant, gnat or other household insect killer or repellent.

Therefore, an ingredient suitable for inclusion in the evaporative cartridges, bottles or packages disclosed herein, or passive dispensers disclosed herein, is a fragrance, air freshener, deodorizer, odor eliminator, malodor counteractant, insecticide, insect repellant, medicinal substance, aromatherapy substance, disinfectant, sanitizer, mood enhancer, or the like, in liquid, oil or gel form, although gels and oils are preferred.

Preferably, if a fragrance is to be dispensed, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals ale known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone or in combination with natural oils are described in U.S. Pat. Nos. 4,324,915, 4,411,829; and 4,434,306, which are incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use with the devices disclosed herein.

Suitable insect repellents, insect attractants and insecticides are well-known and will be apparent to those skilled in the art.

Returning to FIG. 1A, a heater 18 is provided in the form of a metal oxide resistor or wire wound resistor potted in a ceramic block. Of course, other heating devices may be used for the heater 18, such as a PTC (Positive Temperature Coefficient) heater, a coil resistance heater, printed circuitry, an etched foil heating device, or the like. When in use, heater 18 generates heat for heating the active ingredient of liquid or gel formulations stored in a volatile active cartridge 22. Such arrangements of heat-assisted evaporation devices are known in the art, and will not be described in detail herein. In general, however, cartridge 22 contains a formulation/active ingredient whose evaporation rate increases with the application of heat, thus allowing the evaporation rate (and consequently, the potency) to be controlled as the heat is varied.

Preferably, a compartment or recess 23 is provided to receive the volatile active cartridge 22, which is replaceable in the embodiments of FIGS. 1A-1G, 2A-2F and FIGS. 6-31. Any one of a number of known mounting mechanisms may be used to removably secure the cartridge 22 in the compartment 23, but preferably, the cartridge slides into compartment 23, so as to become wedged therein, or snaps into place using a system of mating protrusions and recesses. This allows the user to easily remove and replace spent cartridges, bottles or other devices that serve as reservoirs for containing fragrance oils, with the oils being communicated from the reservoir to the ambient environment with or without a porous wick, or gel cartridges which, when mounted, expose a gel impregnated with fragrance to the ambient environment. If a wick is utilized, a sintered wick as shown at 52d or a conventional porous wick may be employed.

Figure 5A:
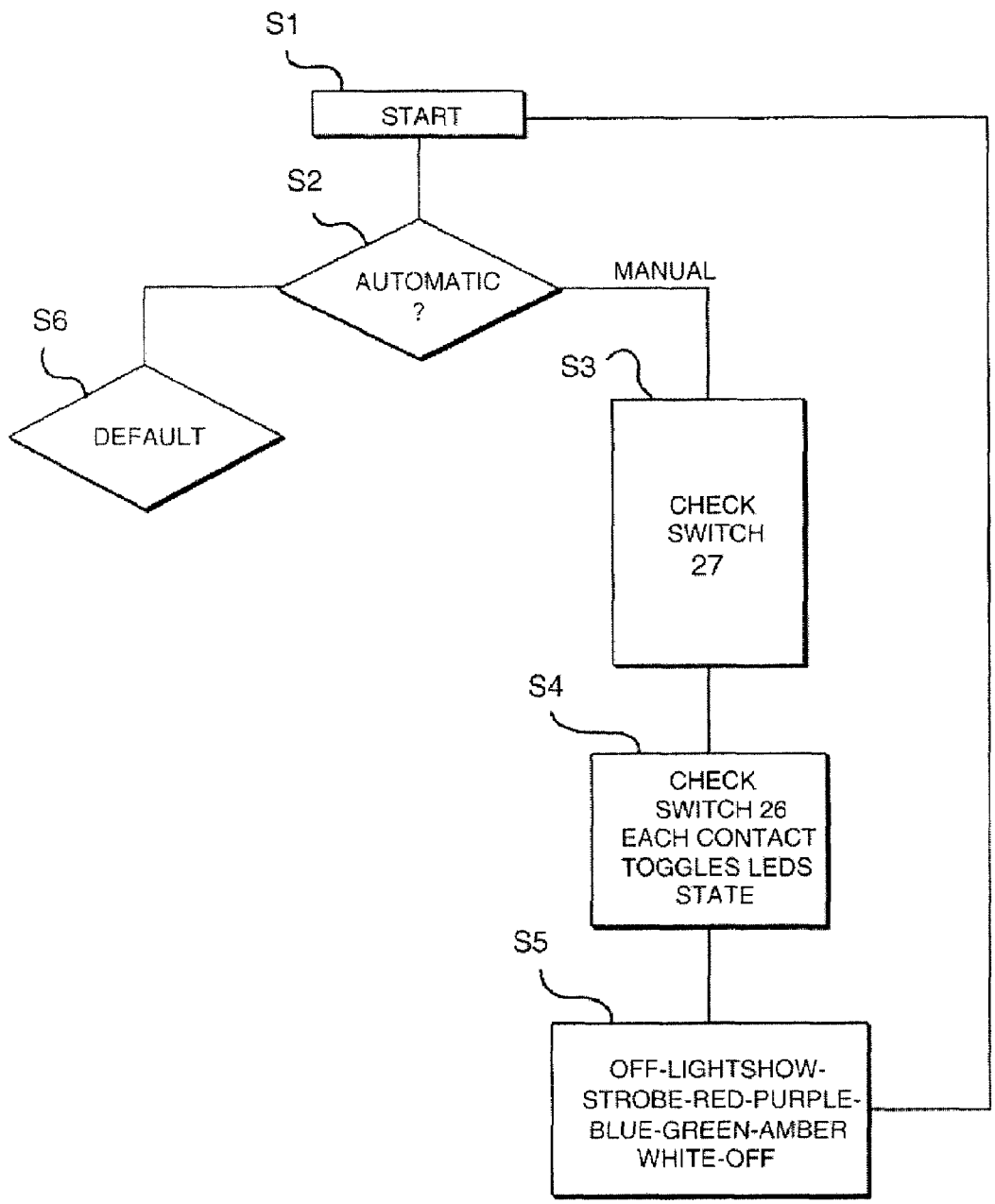
FIG. 5A is a flow chart of a program for operating the devices of FIGS. 1A-1G 2A-2F and 6-35.
Figure 30:
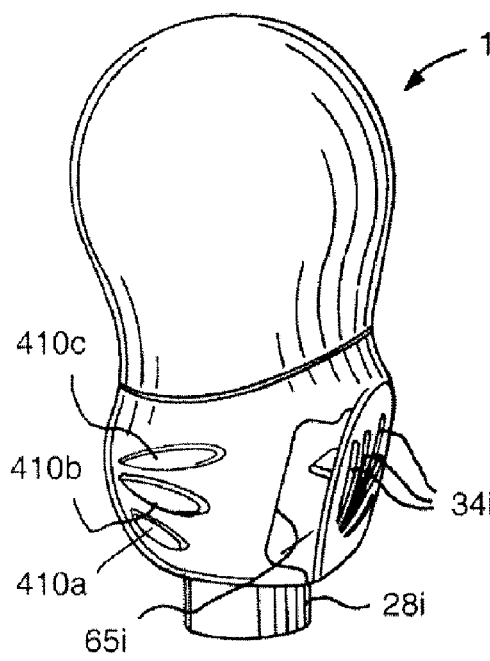
Figure 31:
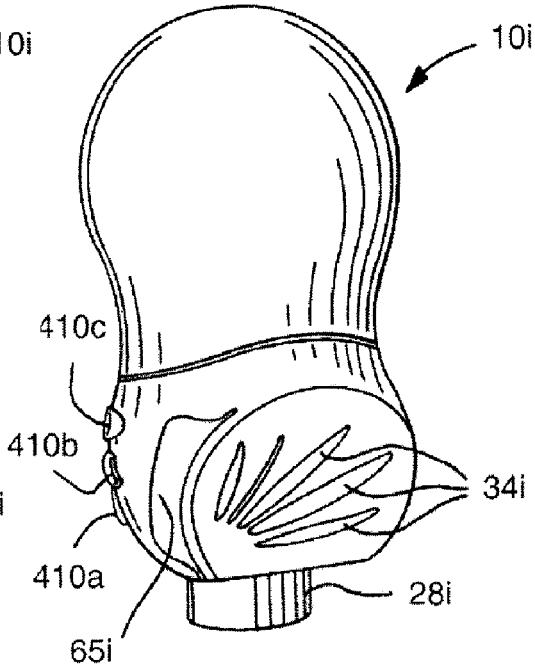
Figure 32:
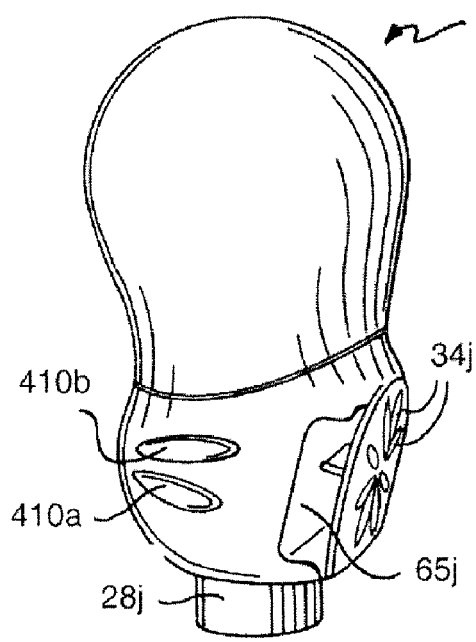
Figure 33:
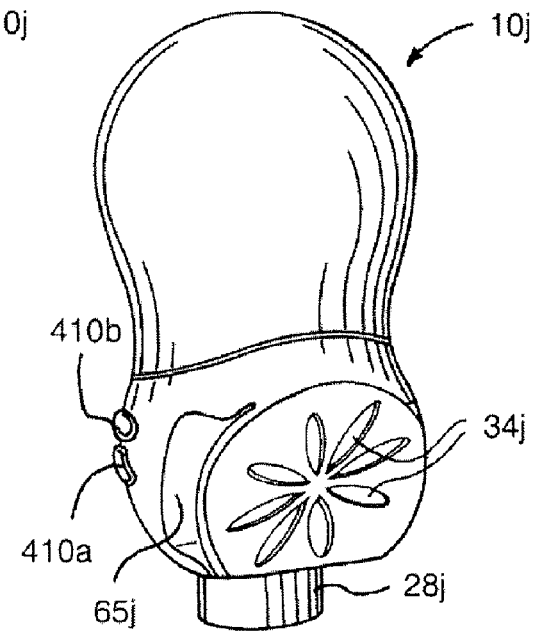
Figure 34:
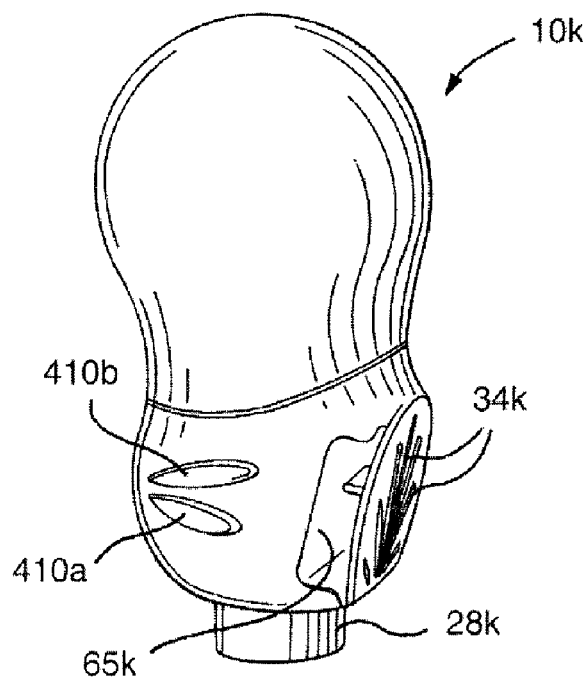
Figure 35:
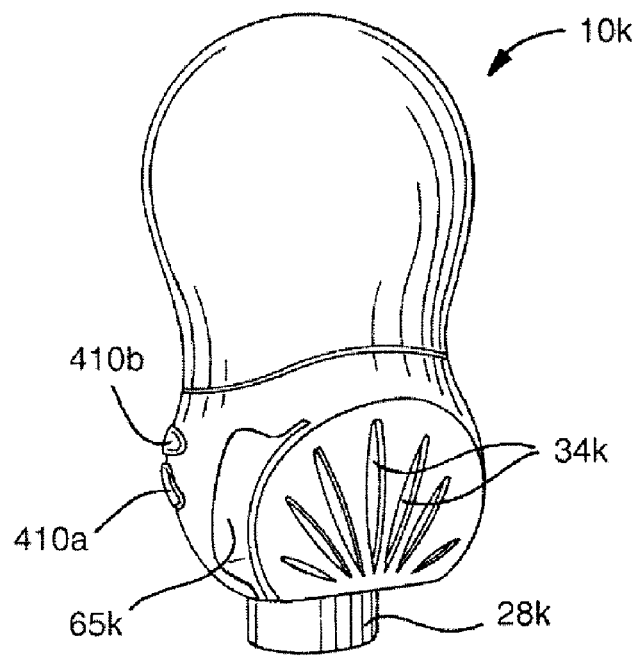

Switch 26 is provided on base 24, to allow a user to control the operation of device 10. Although a switch is shown herein for exemplary purposes, any one of a number of user interfaces may be used so that the user may adjust the setting of the device 10 such as interfaces including one, two, three or more buttons as shown below (see, e.g., FIGS. 5B and 26-31). A lanyard-type switch (FIG. 9-10 and 24-25) may also be employed. Such adjustments made include using a switch or an interface to change the color of the light emitted from the LEDs 14a-14c and 15, adjusting the brightness of the LEDs, switching between white light, colored light, and off settings, scrolling through the various light shows available in the memory of the device, adjusting the evaporation rate of the fragrance (e.g., by adjusting the heat level, when a heat assisted device is used), and/or setting predetermined programs for light shows or fragrance emission changes that may be stored in a memory and operated by a processor (as discussed in more detail below). In preferred embodiments, the user interface is a button or switch that may be toggled to change the operation of the device 10 between different predetermined settings. For example, some suitable user interfaces are described in commonly assigned U.S. application Ser. Nos. 10/561,822 and 11/327,167, which is also incorporated herein by reference. A three button interface is illustrated in FIG. 5C and FIGS. 30-31 below.

FIG. 1B shows another embodiment 10B in which the arrangement of the compartment 23 and heater 18 is altered. The remaining features are the same as those shown in FIG. 1A, and a description thereof will not be repeated here.

FIG. 1C shows another embodiment 10C were in the arrangement of the compartment 23 and heater 18 is the same as that of FIG. 1A but which does not include any colored light capability. Hence, only the white light source 30 and white LEDs 15 are provided. In contrast, FIG. 1D illustrates another embodiment 10D with a single white light source 30 and no colored light sources.

Figure 1F:
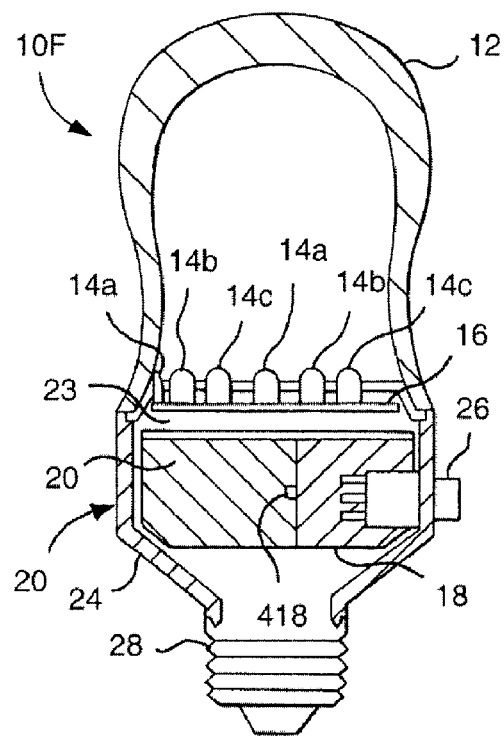
FIG. 1F is a cross-sectional view of another disclosed combination colored light show/active vapor emission device with a threaded, screw-in base.

In contrast, FIGS. 1E-1F illustrate embodiments 10E and 10F with no white light sources and only colored light sources including a single RGB LED group 14a, 14b, 14c as shown in FIG. 1E and two RGB LED groups 14a, 14b, 14c as shown in FIG. 1F.

Figure 1G:
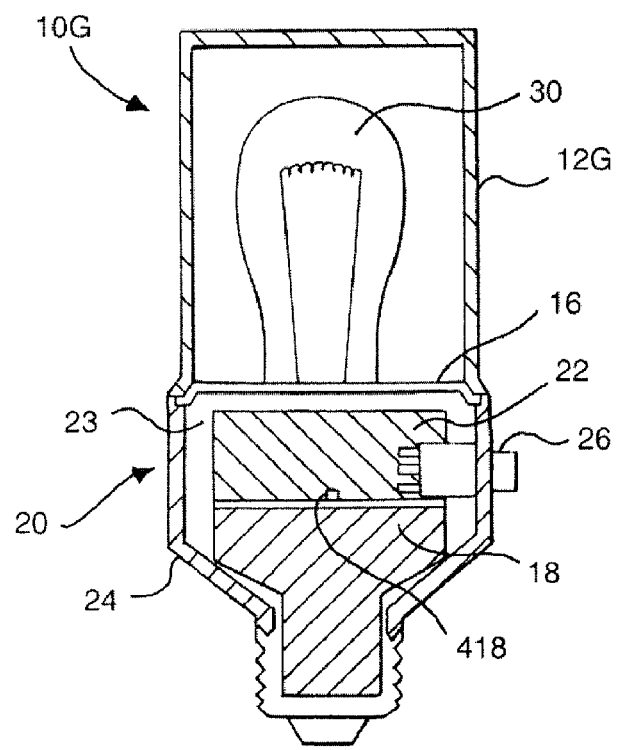
FIG. 1G is a cross-sectional view of another disclosed combination white light/colored light show/active vapor emission device with a threaded screw-in base and wherein only a white light source is provided in combination with an outer cover formed from one or more LCD filters.

FIG. 1G illustrates an embodiment 10G equipped with a single white light source 30G disposed within an outer shell 12G that is fabricated from one or more LCD filters that selectively block certain parts of the light spectrum thereby permitting selected colored light through the outer shell 12G. Thus, the outer shell 12G is linked to the control circuitry of the device 10G that performs the light show function. While flat LCD filters are shown, curved LCD filters are available and are becoming more common.

FIGS. 2A-2F each disclose a pail of devices mateably coupled together for purposes of combining functions. Specifically, referring to FIG. 2A, an assembly 200A is shown with a first device 100A having a threaded male base 128A that is received in a conventional light socket and that includes a volatile active dispenser 123A with a cartridge 122A and heating element 118A. An upper housing 124A is connected to lower base 128A and an open upper end 129A of the housing accommodates a female threaded receptacle 130A. The female receptacle 130A is electrically connected to the male base 128A by a pair of wires 132A, 132A'. The second device 100A' includes a board 116A that supports a white light source 30 and a RGB LED or conventional incandescent colored light cluster 14a, 14b, 14c similar to that shown in the embodiments of FIGS. 1A-1G above. The second device 100A' also includes a switch 126A for controlling the colored light cluster 14a, 14b, 14c and white light source 30.

Figure 2D:
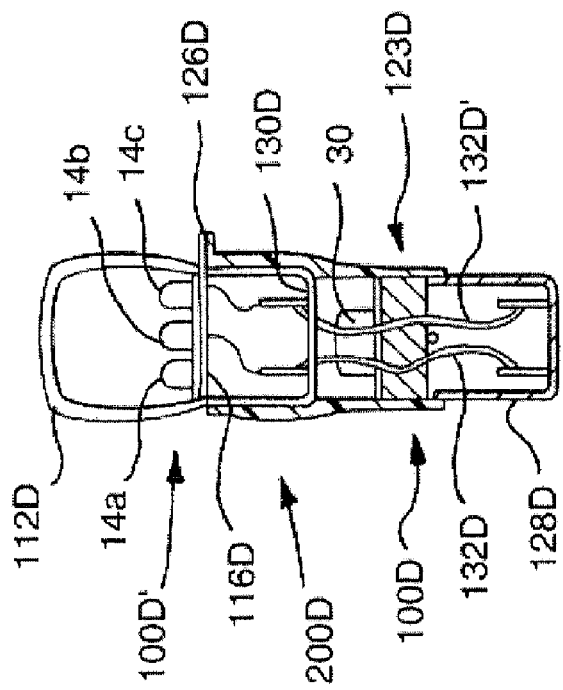
FIG. 2D is a cross-sectional view of a first device or adapter with a plug-in base and equipped with colored light show/active vapor emission capabilities wherein the first device is coupled to a second plug-in device equipped with white light emission capability.
Figure 2C:
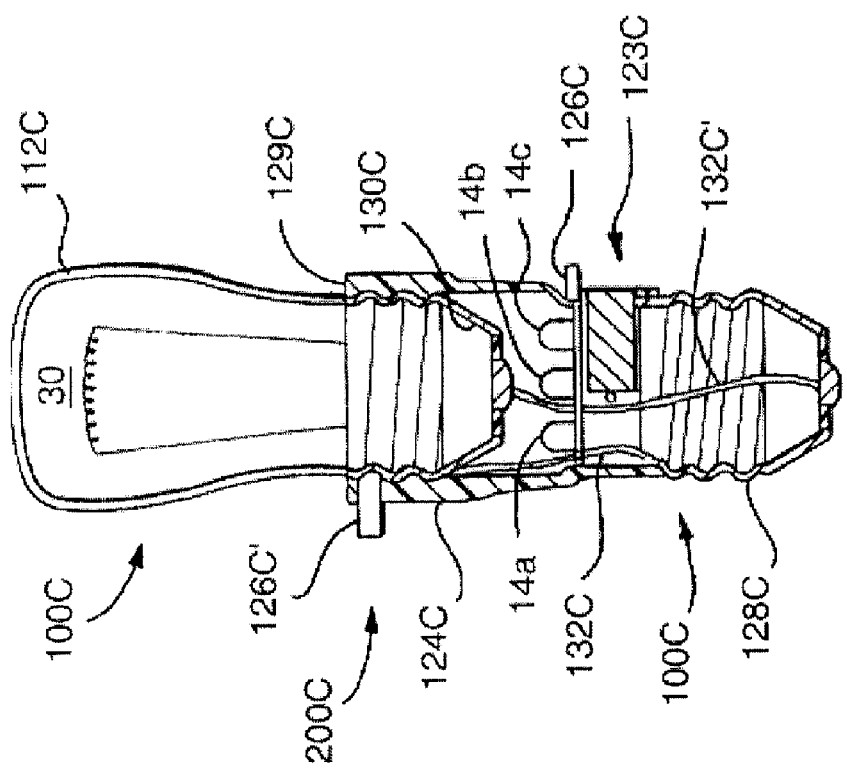
FIG. 2C is a cross-sectional view of a first device or adapter with a threaded screw-in base and equipped with colored light show/active vapor emission capabilities wherein the first device is coupled to a second threaded screw-in device equipped with white light emission capability.

Using the same reference numerals to describe the elements of FIGS. 2B-2F, various combinations of elements in this dual or "piggy-back" arrangement will now be described. Turning to FIG. 2B, the assembly 200B includes a lower device 100B that has a plug-in-type base 128B equipped with an active dispenser 123B, cartridge or active holder 122B and heating element 118B. Holes or vents are shown at 131B for releasing an active. The upper device includes a white light source 30, colored light cluster 14a, 14b, 14c consisting of LEDs or conventional incandescent colored lights and switch 126B. Similarly, the assembly 200C of FIG. 2C illustrates a combination were the lower device includes a volatile active dispenser 123C and colored light cluster 14a, 14b, 14c while the upper device 100 and includes a white light source 30. Because the colored light cluster 14a, 14b, 14c is disposed on the lower device 100C, the lower device 100C preferably includes a control switch 126C. The upper device 100C' my also include a switch 126C' for turning the white light source 30 on and off or for dimming the white light source 30.

Figure 2F:
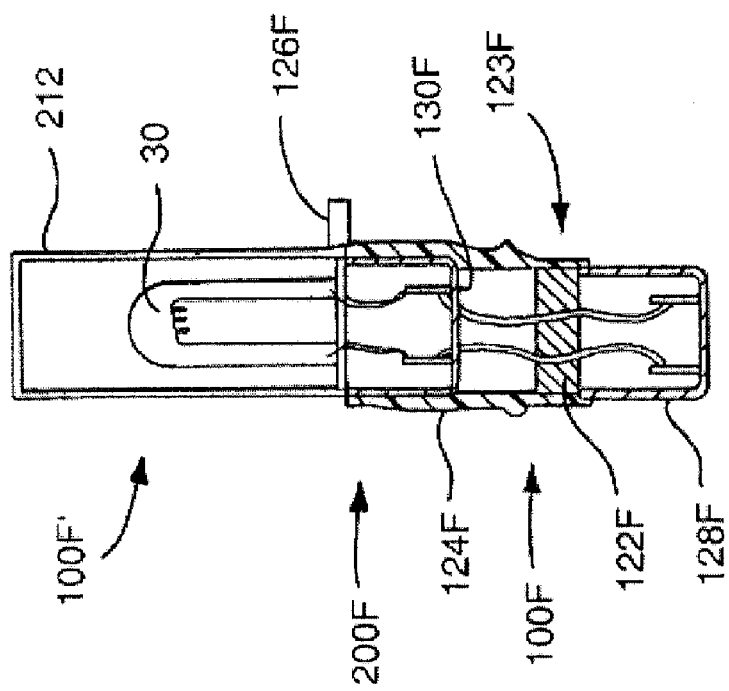
FIG. 2F is a cross-sectional view of a first device or adapter with a plug-in base and equipped with white light/colored light show capabilities wherein the first device is coupled to a second plug-in device equipped with vapor emission capability.
Figure 2E:
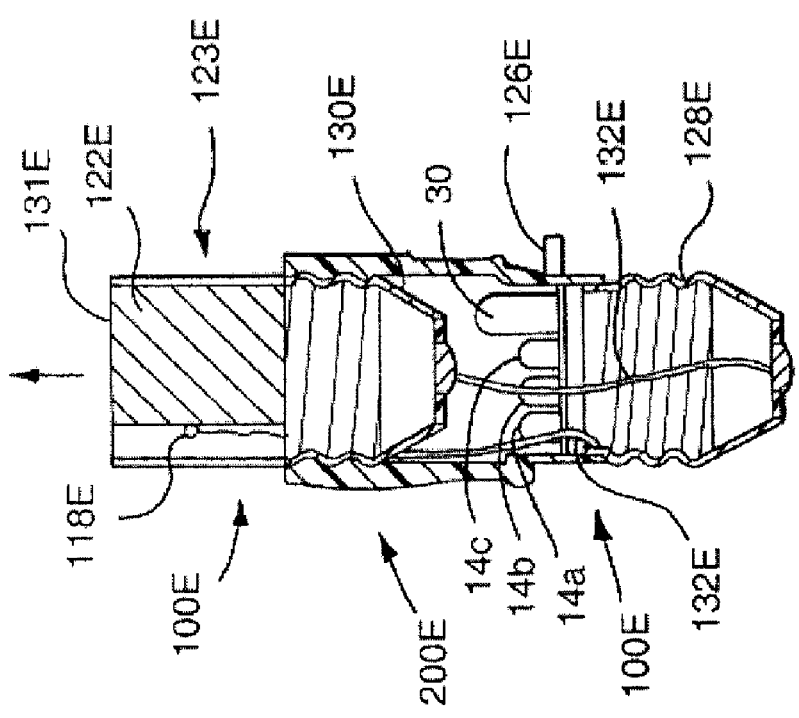
FIG. 2E is a cross-sectional view of a first device or adapter with a threaded screw-in base and equipped with white light/colored light show capabilities wherein the first device is coupled to a second threaded screw-in device equipped with vapor emission capability.

The assembly 200D of FIG. 2D provides a combination whereby the lower device 100D provides a volatile active dispenser 123D and a white light source 30 while the upper device 100D' provides a colored light cluster 14a, 14b, 14c. The assembly 200E of FIG. 2E discloses a combination whereby the lower device 100E provides a white light source 30 in combination with a colored light cluster 14a, 14b, 14c and the upper device 100E' includes a fragrance dispenser 123E and heater 118E. Turning to FIG. 2F, the assembly 200F includes a lower device 100F which features a fragrance dispenser 123F and an upper device 100F' that includes a white light source 30 disposed within a shell 212 formed from one or more LCD filter panels as described above in connection with FIG. 1G above.

Figure 2G:
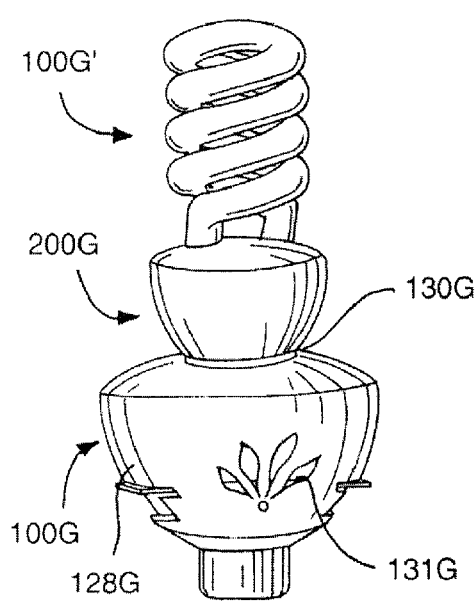
FIGS. 2G-2J are perspective, front, left side and right side views of an adapter that has currently received a coiled fluorescent light (CFL), although it will be noted that other threaded light bulbs may be employed, and wherein the adapter includes volatile active dispensers.
Figure 2H:
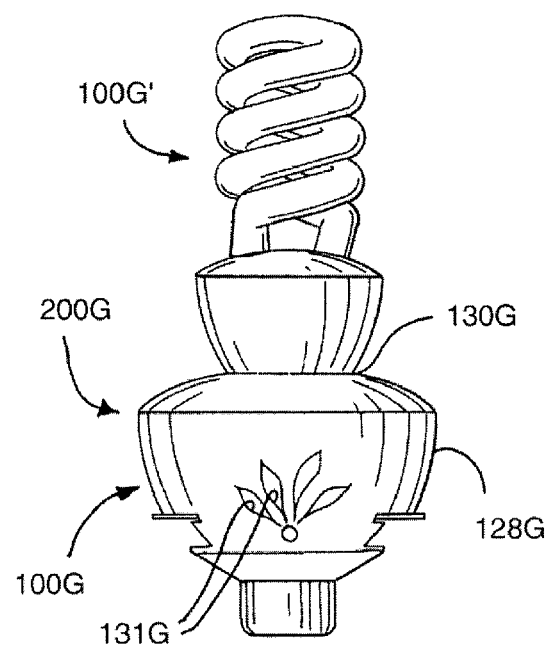
Figure 2I:
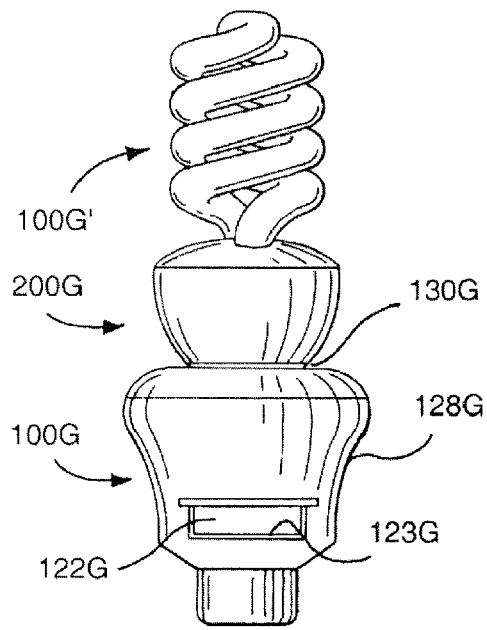
Figure 2J:
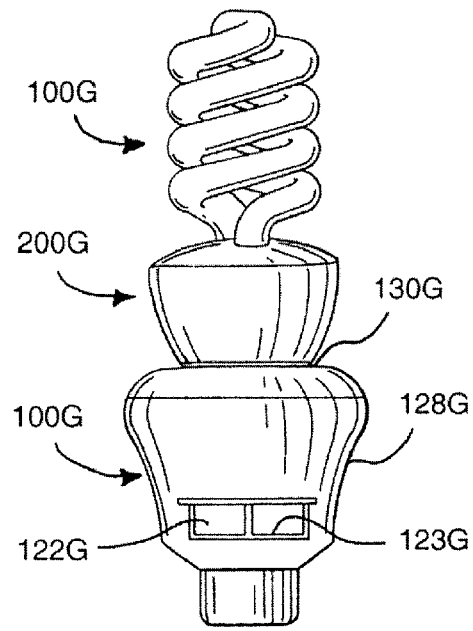

FIGS. 2G-2J disclose yet another alternative embodiment 200G that includes a lower adapter 100G that may or may not be provided with a white light source 100G' that, in this case, is a CFL. Thus, the adapter or lower device 100G may be sold separately. However, it will be noted that the threaded female receptacle 130G is capable of receiving other types of lights, such as incandescent lights and may be a plug connection, rather than a threaded connection. The base 128G includes vents 131G as shown in FIGS. 2G-2H for facilitating the release of volatile active disposed within the cartridges 122G as shown in FIGS. 2I-2J. The base 128G also includes a pair of slots or dispensers 123G for accommodating the cartridges 122G. Other additional features as illustrated above in connection with FIGS. 1A-2F may also be incorporated into the embodiment 200G illustrated in FIGS. 2G-2J.

Figure 3:
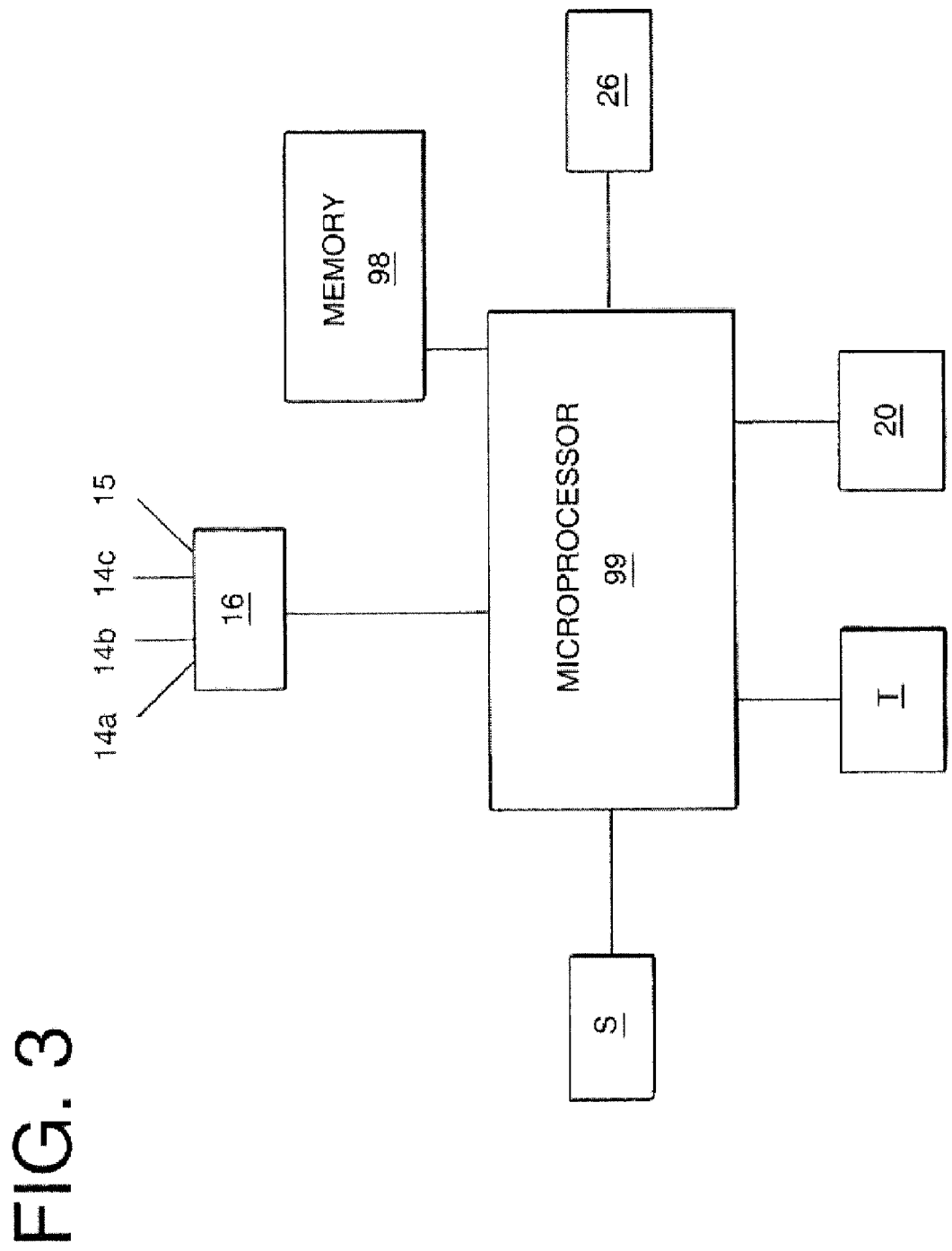
FIG. 3 is a schematic diagram of functional units of the combination white light/colored light/colored light show/volatile active emission devices disclosed herein.
Figure 25:
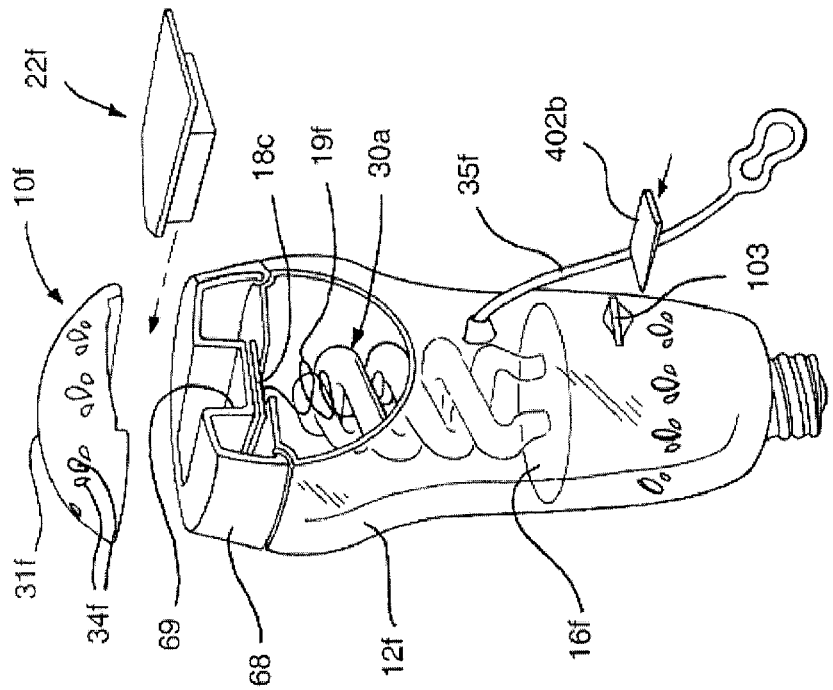
FIG. 25 is a partial sectional an exploded view of the device shown in FIG. 24 particularly illustrating the location of the memory chip and replaceable active ingredient cartridge at the top or upper portion of the outer shell, above the fluorescent lamp and below a vented cover.

FIG. 3 shows a diagrammatic representation of functional units of the device 10 of FIGS. 1A-2J. Microcontroller 99 is a programmable controller that produces output signals to control the emission of light from the LEDs 14a, 14b, 14c, 15 of light array 16, and the amount of active emitted from the dispenser 20. Alternatively, one or more of the control features may be mechanically set by a user without the assistance of a microprocessor. Such basic controls would be readily understood by one of ordinary skill in the art. Preferably, however, microcontroller 99 produces and outputs the signals to operate these devices according to one or more programs stored in the memory 98. The programs may be preset in the memory 98 and then selected and activated by a user through a user interface (e.g., switch 26). Additional light shows may be provided in the form of a supplemental memory chip 102 associated with a replacement cartridge (FIGS. 20 and 22) or a memory chip 102a that is received within a slot 103 disposed in the base (FIG. 25). The signals may be in the form of voltages, coded pulses, of other signals, which control the operation of the components. Alternatively, the switch 26 may set the lighting condition without reference to a stored program.

Operation of microcontroller 99 can also be activated to produce a presentation according to a signal from sensor S. Sensor S may include, for example, a motion sensor, a sound sensor, a timing sensor, an infrared sensor, a power source-monitoring sensor, or the like. If a power source-monitoring sensor is used, the microcontroller 99 may be configured to activate and/or change the presentation of light and/or fragrance when a power switch of a light socket or lamp in which the bulb is received is toggled (e.g., one toggle activates the fluorescent light source 30, two toggles in succession activates the LED array, etc.). Device 10 may also include a timing mechanism T. The timing mechanism T may be an oscillator, crystal, conventional clock, etc. The timing mechanism T may control the operation of microcontroller 99 in accordance with the program from the memory 98. In addition, the timing mechanism T may be used to control the length of a presentation of light, and/or aroma set by a program in memory 98, as programmed by a user.

Control Mechanisms

As discussed above, the components for emitting light and an active may be configured to work in coordination with each other in any one of a number of ways. Provided below are preferred embodiments for configuring and controlling the various disclosed devices to emit light and fragrance. These are, however, only preferred embodiments, and numerous other configurations are possible.

Figure 4:
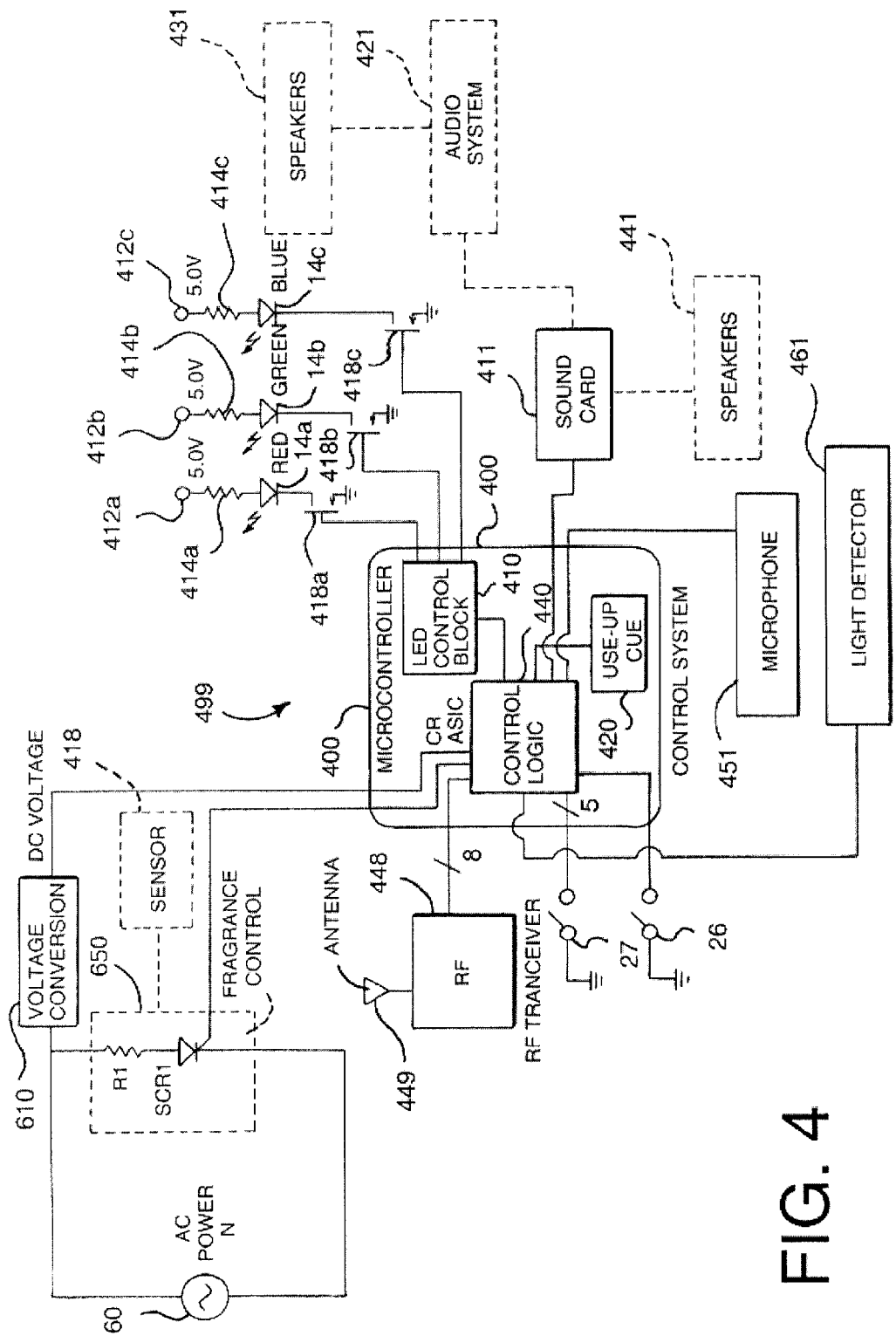
FIG. 4 is a circuit diagram of the control mechanisms for the device is shown in FIGS. 1A-1G and 2A-2F.

FIG. 4 shows a circuit diagram for one control arrangement for operating device 10 that produces a coordinated/combined presentation of light and volatile active. A microcontroller (or ASIC) 400 controls the operation of the device 10.

Power is supplied to the system 499 through a lamp (AC power source 660). A voltage conversion device 610 converts the AC voltage from the AC power source 660 to a DC voltage. A microprocessor 400 receives power from voltage conversion device 610 and controls the operation of system 499 using the received power.

Microcontroller 400 includes a control logic 440 that provides the operational instructions to the various elements of the device 10 in accordance with input signals or internal programs. The control logic 440 converts received signals or runs internal software routines to set the operation of the allay of LEDs 14a-c and/or the volatile active control system 650 (e.g., volatile active dispenser 20), with a resistor R1 acting as the heater.

The control logic 440 sends a signal for controlling the operation of the allay of LEDs to LED control block 410. When using pulse width modulation to drive and control the LED allay, the LED control block 410 sets the duty cycles for the LEDs based on the instruction from the control logic 440.

The control logic 440 may also control auxiliary devices such as a sound card 411, which come in turn, and may be linked to speakers 441 associated with the device 10 or speakers 431 associated with an auxiliary audio system 421. The auxiliary audio system 421 may be a CD player, a computer, or an interface to an MP3 player. Other alternatives will be apparent to those skilled in the art.

Supply lines 412a-412c supply voltage across resistors 414a-414c, from power supply 404. Preferably, the voltage supplied across resistors 414a-414c is between about 3.5 and about 5.0 volts. Resistors 414a-414c in turn power a red LED 14a, a green LED 14b, and a blue LED 14c, respectively. Field effect transistors (FETs) 418a-418c are turned on and off in accordance with the respective duty cycles generated by the LED control block 410. Operation of the FETs 418a-418c control the RGB LEDs 14a-14c to be activated for the portions of the duty cycle set by the LED control block 410. Thus, the intensity and color of the light emitted from the LEDs 14a-14c can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the intensity of the diode appears constant to an observer (with no discernable flicker), until the set period of activation over the duty cycle is changed.

The intensity and exact color of the light emitted from the housing of the device 10 may be varied by changing the current applied to each diode. The different combinations of LED operations will alter the perceived color when the light from the LEDs is diffused to form one perceived color. This is best under stood in connection with FIG. 5B which shows a CIE chart with three coordinates corresponding to three different-colored (RGB) LEDs. The light show as described herein includes starting and ending color points and proceeding along any predefined path between those two points during the course of a show. This is explained in greater detail in pending Provisional Application No. 60/641,441, which is also incorporated herein by reference.

A color point refers to the settings of the LEDs at a given moment of the light show, which provides a specific perceived color. (As the settings of the LEDs change over time in accordance with the instructions for the light show, the color points can ultimately be perceived as a "wash" or "waves" of colors.) Because we are discussing "perceived" colors, the starting color point does not directly correspond to the wavelengths of light emitted by the LEDs used in the color show, inasmuch as those wavelengths are substantially constants. The starting and ending color points can, however, be defined by coordinates on the CIE chart.

The color points can also be defined by the relative intensities of the lights emitted from the LEDs used to produce the color show (i.e., the operational settings for the different LEDs at specified points of the light show). For instance, a color point can be defined by the specific intensity level set at that point in time for each LED being used, and the dominant wavelength of each LED. Preferably, intensity levels will be defined by the pulse widths of the LEDs (e.g., as a percentage of full intensity of the LEDs).

It will be understood by one of ordinary skill in the art that the combination of the lights from different-colored LEDs at specified intensities will directly correspond to a set point on the CIE chart. Therefore, the different possible methods discussed above for defining the color points (i.e., using CIE chart coordinates or specific LED settings) are substantially equivalent for purposes of defining a perceived color.

We note, however, that there are many ways in which the lights from the different LEDs can be combined. In some methods, especially where diffusers are not used and the LEDs are merely placed in close proximity to each other, a user may perceive different colors close to the emission points of the LEDs. When we discuss color points, we refer to the color of a substantially complete mixture of the lights from the different LEDs, even though there may be observable portions of the display in which the user sees distinct colors corresponding to the wavelengths from the individual LEDs, rather than the complete mixture.

The starting and ending color points are similar to the first and last entries in a look-up table setting forth all of the points of a color show in a conventional system; however, instead of providing all of the intervening points from the conventional look-up table, out invention can dispense with the need to determine and stole each and every intervening color point. To achieve this effect, timing information is provided. The timing information defines timing aspects of the light show and LED control.

Using the timing information, a microcontroller may calculate all of the intervening color points for the light show on its own. This saves valuable memory space that would otherwise have to be devoted to complex look-up tables for various light shows. The timing information preferably includes information concerning the duration of the show, from display of the starting color point to the ending color point. The timing information also preferably includes information concerning the tamp speed for the LEDs, either as a whole, or individually. The ramp speed refers to the speed of intensity change of the LEDs. Generally, ramp speed may be defined as the unit of time it takes the LED to change one intensity level (for that particular show), with each intensity level being equal. This can also be defined as the change of intensity per unit of time.

The LEDs may be controlled by pulse width modulation (PWM) such that the pulse width of a constant current applied for a portion of the duty cycle is varied to alter the intensity of the light emitted from the LED. The intensity level of the LED can be measured as a fraction of the duty cycle during which the constant current is applied, which, among other ways, can be expressed as a percentage. When an LED is not on, the pulse width is at 0%. When a constant current is applied to the LED for half of the duty cycle, the intensity of the LED is at 50%. Ramp speed maybe defined as the amount of time between changes of intensity of one percentage point of total intensity. Consequently, if the ramp speed of an LED is set at two seconds, then during the course of the light show that LED will change its intensity by one percentage point every two seconds until reaching the target value (i.e., the intensity value of the LED for achieving the ending color point). In an embodiment, ramp speed is defined as the percentage change per second. Of course, the speed can be defined in any one of a number of ways, as would be understood by one of ordinary skill in the art. Also, the lamp speed can be a positive or negative value, depending on whether the intensity of the LED is to be increased or decreased during the light show. Alternatively, the microcontroller 400 can be programmed to increase or decrease the intensity setting by comparing the starting intensity setting to the ending intensity setting. Thus, for instance, if the microcontroller 400 determines that the value of the ending setting is lower than the value of the starting setting, the microcontroller 400 will decrease the intensity of the LED at a rate set by the given ramp speed.

Figure 5B:
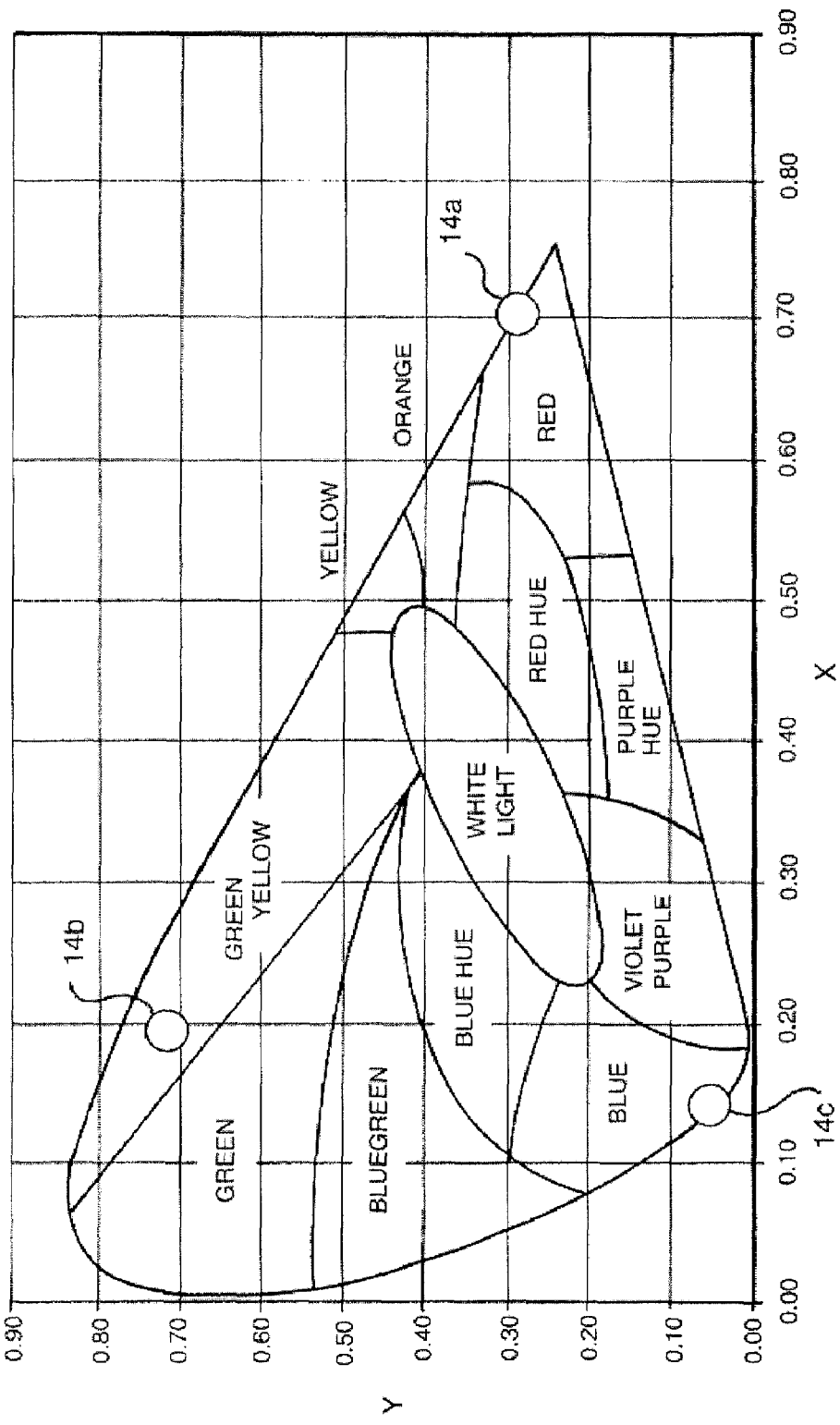
FIG. 5B shows an exemplary CIE chart with three coordinates corresponding to three LEDs of different colors, red, green and blue, wherein a light show presented in accordance with this disclosure comprises any path disposed within the boundaries of the curve carried out over time.
Figure 5C:
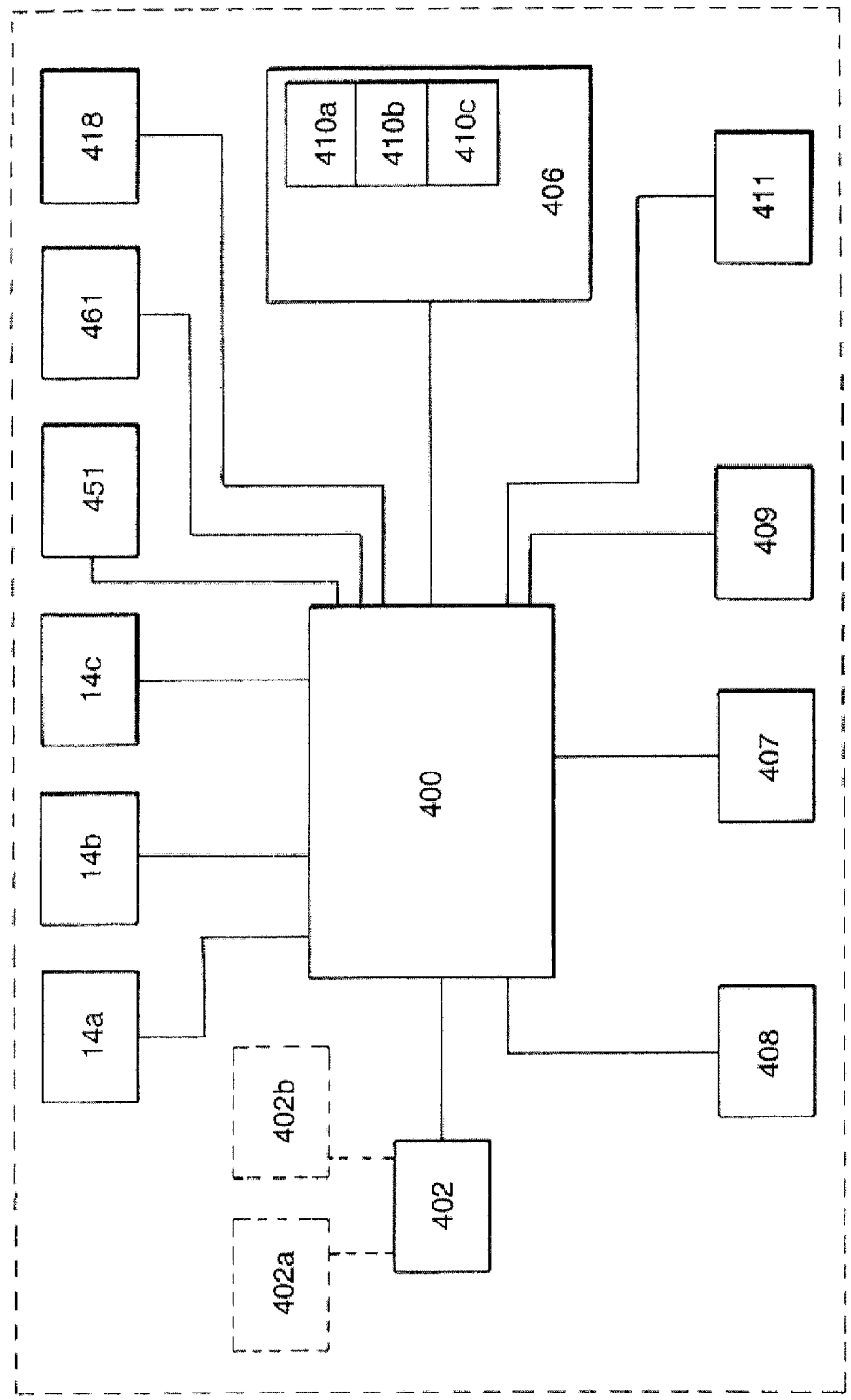
FIG. 5C is a schematic drawing of the control mechanism for various devices shown in FIGS. 1A-1G, 2A-2F and 6-35.

With the timing information provided, the microcontroller 400 controlling the LEDs 14a-14c can be provided with logic that calculates the intervening color points between the starting and ending points of the CIE chart of FIG. 5B. The logic reads the timing information from memory and adjusts the duty cycle for each LED in accordance with the ramp speed and target intensity. The intensity for each LED is adjusted until the target value is reached or the duration of the show has been reached. At this time, the microcontroller 400 will read the next set of timing information from memory and begin again. Of course, if the target intensity is reached prior to the duration of the show, the microcontroller 400 will hold the intensity of the LED until the duration is reached. If a continuously changing show is desired, the tamp speed may be set such that the target intensity is not reached prior to the duration of the show and thus, the target value will never be reached. Likewise, the microcontroller may be configured to ignore the duration, and load the next intensity and ramp speed as soon as the target intensity is reached.

The programming for achieving this would be readily understood by one of ordinary skill in the art. Accordingly, a detailed description of the many different ways of programming the microcontroller will not be provided herein.

While three colored LEDs 14a, 14b, 14c are shown with respect to the device 10 in FIGS. 1-2, any number of LEDs or RGB LED clusters may be used. In addition, the choice of which color LEDs to provide may be dictated by design preferences. Further, the use of LEDs is not necessary as incandescent or conventional colored light sources may be employed using the same techniques as described above.

Generally, one of each colored light will be provided in close proximity to the other colored lights. With such a cluster arrangement, the exact color of each light of the set of three different colors can be adjusted to create a blended color, for example, amber or purple. This blending can be achieved by providing the three lights in such close proximity that the observer only sees the blend of colored lights, rather than each individual colored light. Alternatively, or in addition, a diffuser may be provided to diffuse the light of the three lights to produce the combined color. In other embodiments, the lights may be projected off of a surface to be combined before being viewed by an observer. When the LEDs are not placed close to each other, or there is not sufficient diffusion, multiple colors may be perceived in the device 10. This is a matter of design preference.

LEDs and incandescent light sources are readily available from lighting manufactures in a wide variety of colors. Also, the arrangement and operation of LEDs or other types of colored light sources to achieve a desired presentation will be apparent to one of ordinary skill.

Turning to FIG. 4, the microprocessor 400 may monitor the temperature delivered to the active cartridge 22 through the use of a temperature sensor 418 (see FIGS. 1-2, 4 and 5C). In this case, the microprocessor 400 can adjust the current through the heating resistor R1 to keep a constant temperature to the active cartridge 22, 122 regardless of the orientation of the bulb or fixture used. Thus, the proper amount of heat is provided to the cartridge 22, 122 regardless of the type of white light source (incandescent, fluorescent, coiled fluorescent or white LED) or the orientation of the white light source. The sensor 418 provides feedback to the microprocessor 400 so the correct temperature of the cartridge 22, 122 is maintained. Different fragrances and different actives such as different insecticides or insect repellents will require different temperatures for proper emission rates.

Additionally, the temperature sensor 418 and microprocessor 400 may adjust the heat to deliver more fragrance or active at one point in a particular light show and less fragrance or active at a different point or time in a particular light show to enhance the user experience. For example, certain color schemes of the light show may require more or less fragrance or active than other color schemes of a light show. By way of one example that is not intended to be limiting, it may be beneficial to emit more fragrance during a blue/green portion of the light show and less fragrance during a red/orange portion of the same light show. Other active emission rates can be controlled according to a light show or according to other outside sources such as exterior light or sound as recorded by a microphone 451 or a light detector 461 is indicated in FIG. 4.

Figure 22:
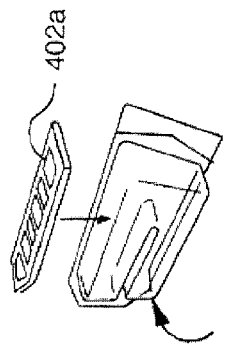
FIG. 22 is an exploded view of the memory card and active ingredient replacement cartridge shown in FIG. 20.

Further, in the case where a memory card 402 is disposed on the active cartridge 22 such as the memory card 402a and the active cartridge 22e shown in FIG. 22, the memory card 402a may contain temperature information that is communicated to the microprocessor 400 that, in turn, is used to set the optimum temperature for that active optimize release of the active.

White LEDs 15 or more preferably a fluorescent bulb 30 may be connected to control block 410, or may be controlled through separate means, inasmuch as the white LED(s) (or other conventional white light source) is typically either on or off and is not necessarily subject to the same range of control (unless dimmers or the like are used). Such modifications, however, would be readily understood by one of ordinary skill in the art.

The microprocessor 400 may also send a control signal to volatile active control 650, as shown in FIG. 4. In this embodiment the volatile active dispenser being controlled is an evaporative-type dispenser. A resistor R1 is heated by a current passing across the resistor R1. Typically, the resistor R1 is placed adjacent to an area at which a volatile active-containing gel or oil is exposed to air and the heat from the resistor R1 causes the volatile active to be vaporized. A switch SCR1 varies the current passing across the resistor R1, thus varying the heat produced by resistor R1 and the rate of vaporization of the volatile active. In alternative embodiments, the resistor R1 may be replaced and/or supplemented by a fan which is controlled by switch SCR1, or an atomization device. Also, switch SCR1 may be replaced by an FET in other embodiments. Further, the volatile active dispenser may also be mechanically adjusted by a user, rather than through a microprocessor.

Figures 28, 29:
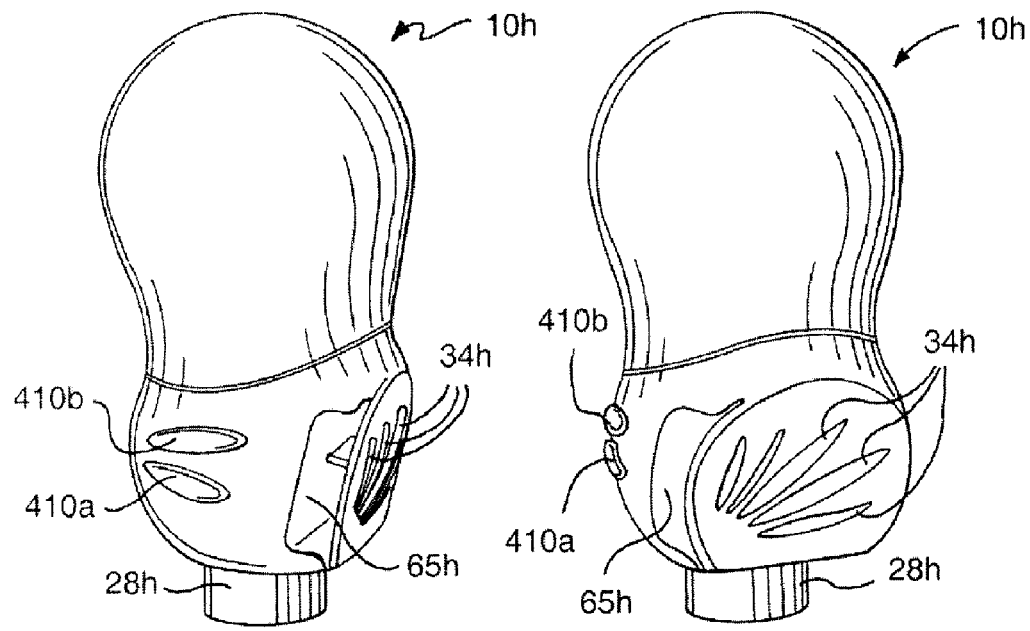

Microprocessor 400 may also control a use-up cue 420. The use-up cue 420 tracks the use of volatile active control to estimate the time at which the volatile active in the volatile active dispenser is likely to be used up. When the use-up cue 420 determines that volatile active has been spent, it sends a signal to LED control block 410 to cause the LEDs to illuminate in a pattern, color, or other manner to indicate to a user that it is time to replace the volatile active in the dispenser if a refillable dispenser is used, or more preferably, the volatile active cartridges shown at 22 (FIGS. 1-2), 22a (FIGS. 7-8), 22b (FIGS. 10-12), 22c (FIG. 15), 22d (FIGS. 18-19), 22e (FIGS. 20-23), 22f (FIG. 25) and 22g (FIG. 28). A large variety of cartridge-type containers, bottles or inserts may be utilized for the "cartridges" 22 disclosed herein. Various other designs embodiments will be apparent to those skilled in the art. Further, suitable means for determining or communicating to the use-up cue 420 when a particular cartridge 22 is empty or near-empty will also be apparent to those skilled in the art. A simple resistance mechanism may be desirable due to low-cost and dependability.

Returning to FIG. 4, the control logic 440 may be programmed/controlled in any number of ways. In one embodiment, an RF transceiver 448 receives an external signal, through an antenna 449, from a remote control. That signal is transmitted from the RF transceiver 448 to control logic 440 to set the presentation of light through the LED control block 410 and the volatile active control 650. Also, the operation of the control logic may be set by an internal program.

A user may manually set the volatile active output and light show. In this case, a program select switch 26 (FIGS. 1-3) may be operated by a user to set a light show program for the LEDs 14a-14c. In this embodiment, a switch 27 (FIG. 5A) is also provided to control a volatile active level to be dispensed.

Of course, additional buttons or switches may be provided, depending on the level of the control and programmability desired. In particular, a switch can be provided to control whether manual or automatic operation/programming is desired as discussed in connection with FIGS. 5C and 26-35 below.

FIG. 5A shows one program for operating the control system shown in FIG. 4. One of ordinary skill in the art will appreciate that a wide variety of other programs may also be implemented to produce the desired control over the presentation of coordinated light and aroma. The program starts operation of the device at step S1. At step S2, it is determined whether operation of the microcontroller 400 is to be set manually by a user or automatically with a particular program. If manual operation is selected, the program proceeds to step S3. In step S3, the setting of the switch 27 is checked to set the level for operating the heater 18. For instance, in a first switch setting, the heater 18 is operated at a first temperature, while other temperatures may be set by other settings. In step S4, the operation of the switch 26 is checked. The system is set such that different preprogrammed light shows are selected depending on how many times a user toggles the switch 26. Step S5 sets the light show from among an off setting, a variant light show, a strobe setting, emission of red light, emission of purple light, emission of blue light, emission of amber light, and emission of white light, depending on the toggling of switch 26.

If the automatic mode is set in step S2, the program proceeds to step S6, in which a default setting is provided for operation. This automatic setting may be set by information from a program set in the memory, a sensor reading, a remote control, the power supply (e.g., by toggling a light switch controlling the lamp in which the device 10 is positioned), or the like.

Turning to FIG. 5C, a schematic drawing is provided of another system, which includes a microcontroller 400, a memory 402, three LEDs 14a, 14b, 14c, a user interface 406, a power source 407, a clock mechanism 408 and a USB port or other type of input port 409. FIG. 5C also discloses a sound card 411, a microphone and 451 and a sound attacker or proximity sensor 461. Thus, the system can be coupled to an exterior auxiliary audio system 421 as illustrated in FIG. 4. Speakers 441 may be incorporated into the device 10 (see the speakers 441 of FIG. 4) or associated with the auxiliary system 421 (see the speakers 431 of FIG. 4).

Microcontroller 400 may be an Amtel Mega8 processor. Memory 402 preferably is Microchip 24LC00 (manufactured by Microchip Technologies, of Chandler, Ariz.) or an Amtel AT25F512 (manufactured by Amtel Corp., of San Jose, Calif.). In other embodiments the memory 402 may be a memory chip or card 402a or 402b (see FIGS. 20, 22, 24, 25) detachable from the device and microcontroller, so that the light shows stored therein may be removed and replaced with other memory cards/chips 402, 402a. In this manner, the user can purchase new light shows and/or coordinate the light shows with the particular active ingredient that is being emitted.

Preferably, the memory 402 will store data concerning the light show, as discussed above. This data may include starting color points, ending color points, duration information for segments/shows, ramps speeds, other timing information, and the like. The microcontroller 400 may have onboard program memory or external program memory containing the instructions for interpreting the light show data, calculating intervening light points, and controlling the LEDs based at least in part on the color data and timing information. Thus structured, memory 402 storing the light shows does not need the full range of data typically provided in look-up tables used to define light shows.

The size of the external memory 402a, 402b and extent of the program stored therein to instruct the microcontroller 400, and the extent of the program stored onboard the microcontroller 400 in the manufacturing process can be determined based on design needs. Also, in future replacement memory cards 402, where such are used, additional logic can be provided to control the microcontroller 400, when additional information is needed to operate the new light shows. One of ordinary skill in the art would appreciate the different ways of dividing up such information between the memory 402 and microcontroller 400. However, in a preferred embodiment, the system is defined such that microcontroller 400 contains the operating instructions for the light shows and the memory 402 contains the operating instructions for the light shows and the memory 402 contains the timing, intensity and ramp speed data for each LED used in the light shows.

When multiple light shows are provided in one memory 402, it is preferable that the device in which the memory 402 is mounted be provided with a user interface 406 to allow the user to switch between shows. In this embodiment, user interface 406 includes three buttons 410a, 410b and 410c which allow the user to switch between different settings. The different settings may be on/off states, rotating or scrolling through the different light shows, a freeze function to stop a show in progress or hold a show in progress, operating the booster heater or heater for the active ingredient cartridge or bottle and turning the fluorescent lamp on/off. A fan (not shown) may also be included to assist in the emission of and distribution of the volatile active.

Numerous other user interfaces 406 may be provided, as would be understood by one of ordinary skill in the art. For instance, a remote control 406a (wireless or wired; see e.g. FIGS. 13 and 23) may be provided to control the device 10 from a remote location. Because the programming and mechanics of remotes and other possible user interfaces are known in the art, a more detailed description will not be provided herein. It will be noted, however, that the remote control 406*a* may be detachably connected to the device by a known mechanism, such as a hook and loop fasteners, a magnet, adhesive, etc.

Additionally, a portion of the program memory containing the light show data onboard the microcontroller 400 may be reprogrammed with new light show data via a standard personal computer through the serial or USB interface 409. The user interface 406 may also consist of a conductive coating that responds to the user's touch, a rotary switch, a push button switch, or a mechanical switch that is actuated by pressing on the device 10.

Figure 5D:
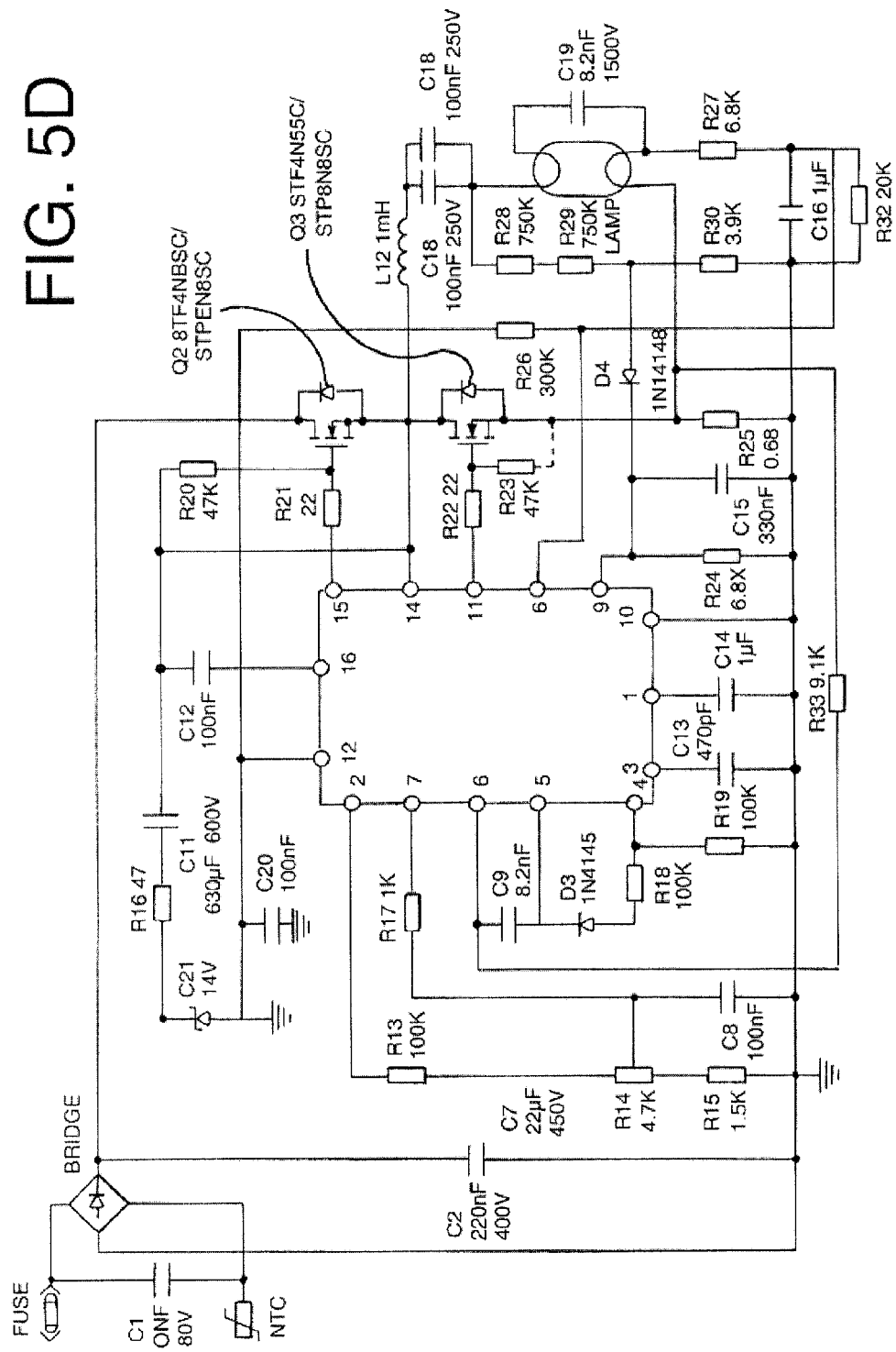
FIG. 5D is a circuit diagram of the ballasts for the coiled fluorescent lamp (CFL) white light sources of the devices shown in FIGS. 1A-1G, 2A-2F and 6-35.

A circuit diagram for a dimming ballast for a coil the fluorescent light bulb 30 (see FIGS. 6-35 below) is shown in FIG. 5D. Of course, other ballast designs will work and will be apparent to those skilled in the art. FIG. 5G shows a circuit diagram for the L6574 processors shown in FIG. 5D. The L6574, as shown in FIG. 5G and which is available from ST Microelectronics (www.st.com), includes a dedicated timing section enabling the parameters for proper pre-heat and ignition of a fluorescent lamp to be set. Further, the L5674 also includes the OP AMP (FIG. 5G) for implementing closed loop control of the lamp current during operation thereby enabling the user to dim the white light source 30. Returning to FIG. 5D, the pin connections for the L5674 are as follows: (1) preheat timing capacitor; (2) maximum oscillation frequency setting; (3) are so later frequency setting capacitor; (4) minimum oscillation frequency setting resistor; (5) operational amplifier for purposes of implementing a feedback control loop; (6) converting the input of the operational amplifier; (7) non-inverting the input of the operational amplifier; (8) enable 1 which forces the device in a latched shut down state under predetermined voltage conditions; (9) enable 2 which restarts the start-up procedure; (10) ground; (11) low side driver output; (12) supply voltage; (13) not connected; (14) high side driver floating reference; (15) high side driver output; and (16) bootstrapped supply voltage.

Figure 5E:
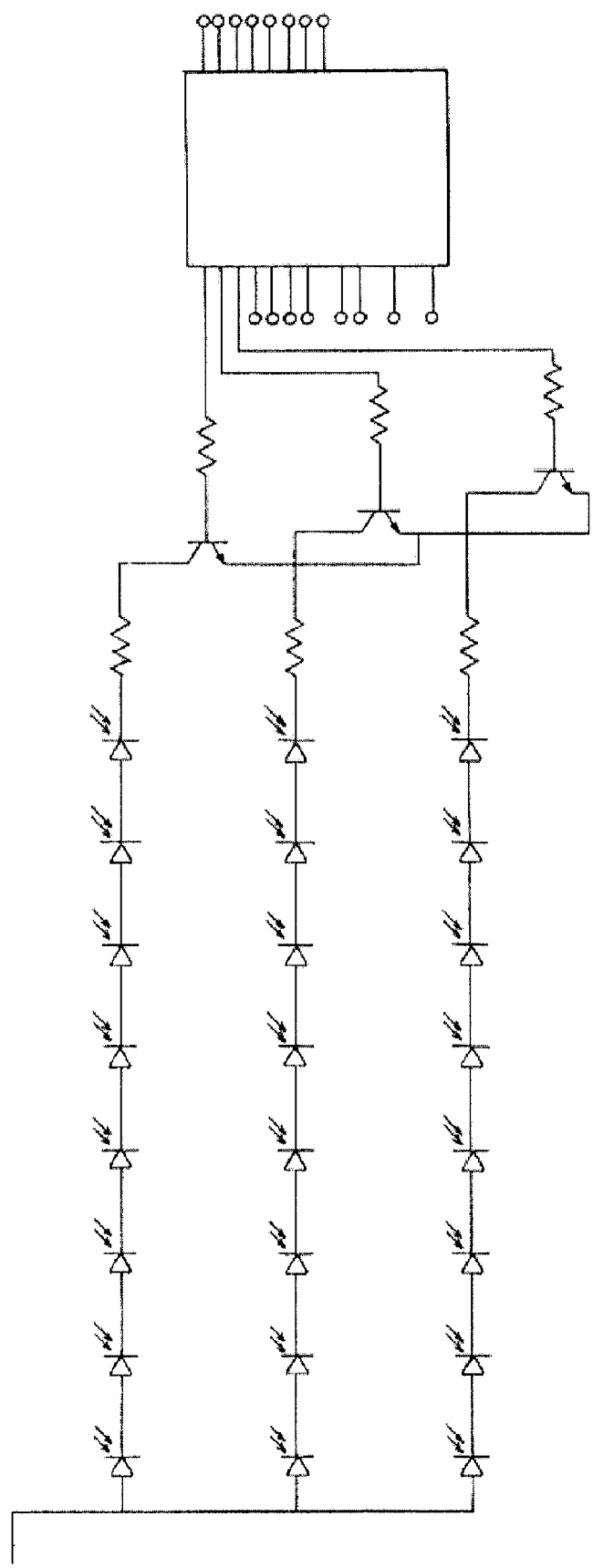
FIG. 5E is a circuit diagram for the LED drivers for the devices shown in FIGS. 1A-1G, 2A-2F and 6-35.
Figure 5F:
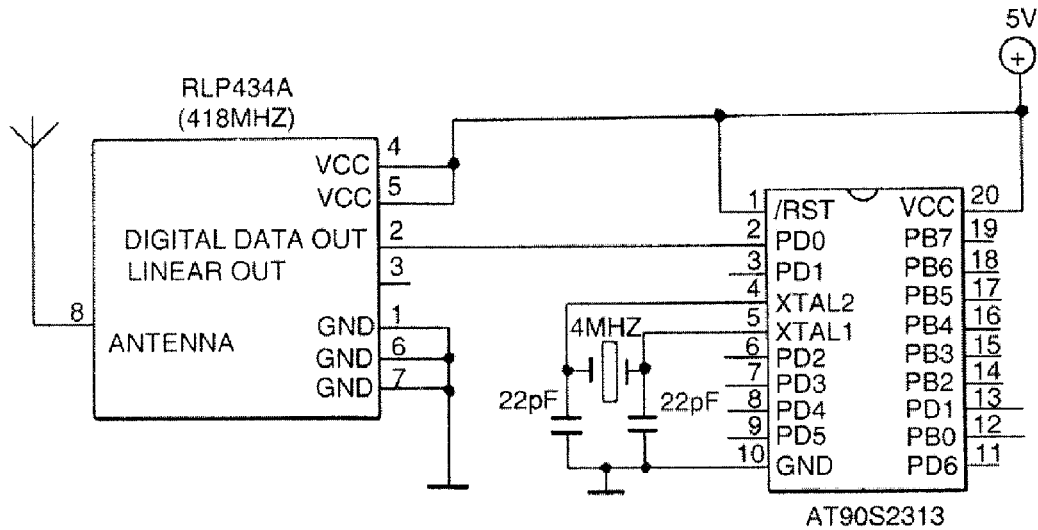
FIG. 5F is a circuit diagram for the radiofrequency (RF) receiver for the devices shown herein employing a remote control (e.g., FIGS. 9-13 and 20-23 below).
Figure 5G:
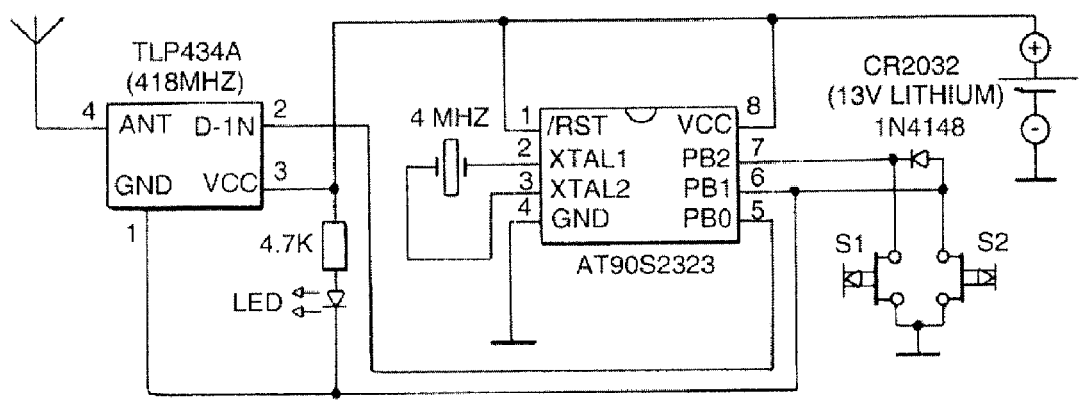
FIG. 5G is a circuit diagram of for the RF transmitter for the devices shown herein employing a remote control (e.g., FIGS. 9-13 and 20-23 below).
Figure 5H:
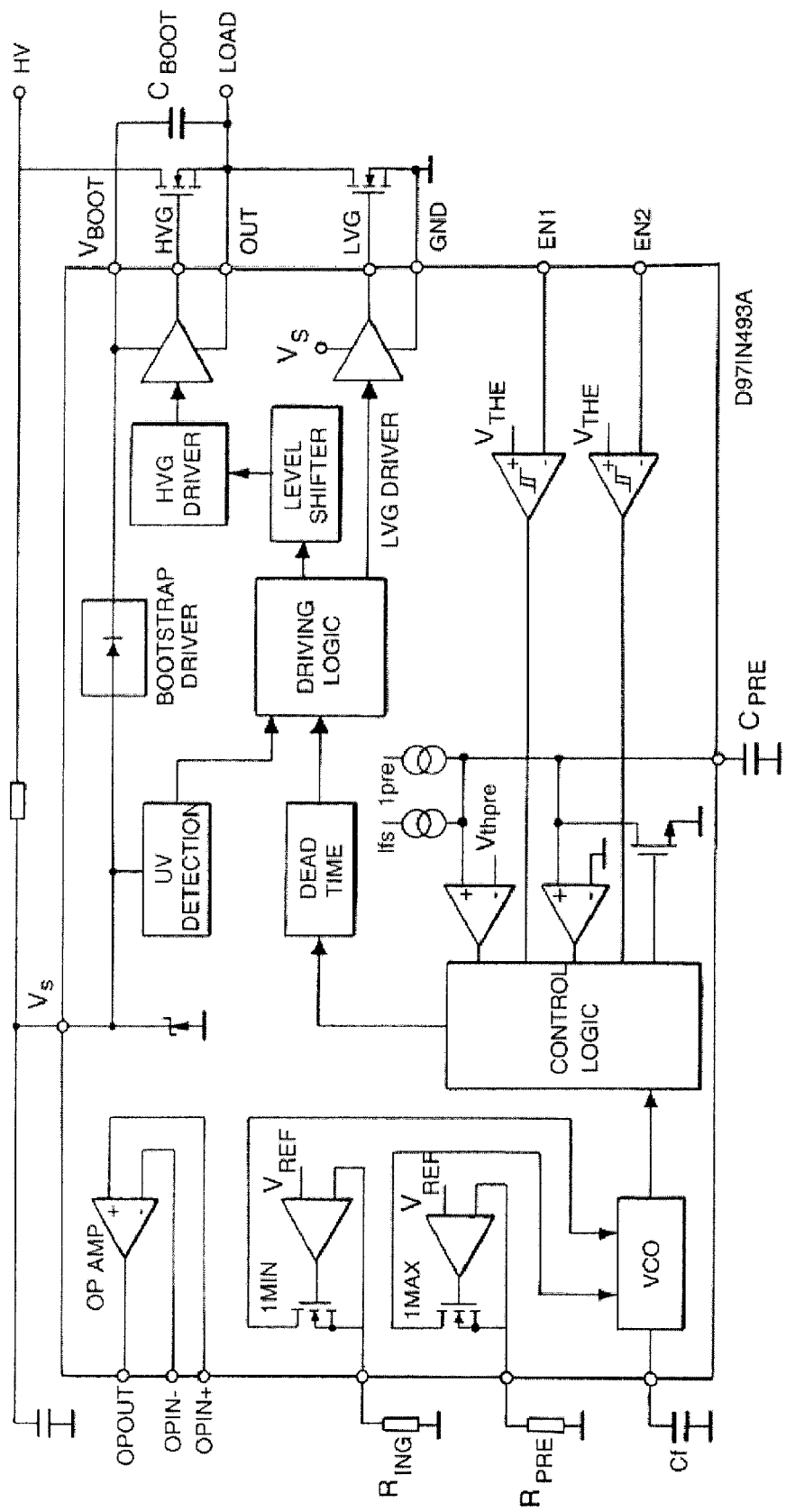

An LED driver circuit is shown in FIG. 5E. The driver circuit shown in FIG. 5E is controlled by the microcontroller 400. For those embodiments employing a remote control 406 (see FIGS. 5C, 9-13 and 20-23 below), a suitable RF receiver circuit diagram is shown in FIG. 5F and a suitable RF transmitter circuit diagram is shown in FIG. 5G.

Alternative embodiments to the device 10 are illustrated at 10*a*-10*g* in FIGS. 6-31. FIGS. 6-8 illustrates a first alternative embodiment 10*a*. In FIG. 6, the outer shell 12 includes a top 31 that, as shown in FIG. 7, is connected to and supports an active ingredient cartridge 22*a*. The cartridge 22*a*, as seen in FIG. 8, is semi-cylindrical and cross-section includes a semi-cylindrical shell 32 which is covered by a permeable membrane 33. The permeable membrane 33 permits the migration of active or volatile active through the membrane 33 and into the chamber or space 34 defined by the outer shell 12*a*. The volatile active then exits through the vents shown at 34.

In the embodiment 10*a*, a switch is provided in the form of a cylindrical ring 35. Rotation of the switch 35 in the direction of the arrow 36 permits the user to switch between a white light function where the fluorescent lamp 30*a* is generating light to a function where a colored light show is being performed using the circuitry and elements discussed above in connection with FIGS. 1-5*c*. A pair of electrical connectors 37 is provided at the lower and 38 of the cartridge 22*a* for being mateably received in the holes 39 disposed in the LED board 16*a* for connection to a heating element (not shown) and/or the connectors 37 can also be used to communicate with the microcontroller 400 to match or coordinate the light show with the fragrance contained within the cartridge 22*a*. Air vents or finger grips may be provided at 41 in the base 24*a*. These elements may also be purely decorative in nature. Various LEDs are shown on the board 16*a* generally at 14.

Turning to FIGS. 9-12, another device 10*b* is disclosed. The outer shell 12*b* is connected to a ring of replacement cartridges shown at 22*b*. In this embodiment, as shown in FIG. 12, the shell 12*b* and replacement cartridges 22*b* form a replacement kit 42. The lower edge 43 of the shell 12*b* is irregular in shape for aesthetic purposes primarily and mates with the corresponding edge 44 of the base 24*b*.

The base 24*b* is equipped with a lanyard-type switch 35*b* which may be supplemented with a replaced by the remote control device shown at 406*a* in FIG. 13. Vents are shown at 34*b* in the base 24*b* for releasing volatile active from the cartridges 22*b*. In the embodiment 10*b*, additional heat may not be necessary due to the proximity between the cartridges 22*b* and the board 16*b* but a heating element can be conveniently disposed at or near the board 16*b* for purposes of encouraging or controlling active emission from the cartridges 22*b*. Turning to FIG. 11, the cartridges 22*b* consist of a continuous series of outer shells 46 separated by a series of spaced-apart indentations 47 with chambers enclosed by the permeable membrane 33*b*. The remote control 46 may include a plurality of buttons and have functions similar to those described above in connection with the interface 406 of FIG. 5C.

Figure 16:
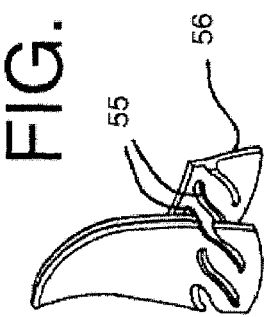
FIG. 16 is a partial exploded view of a portion of the outer shell and elastomeric finger or thumb grip that extends through slots disposed in the lower portion of the outer shell.
Figure 15:
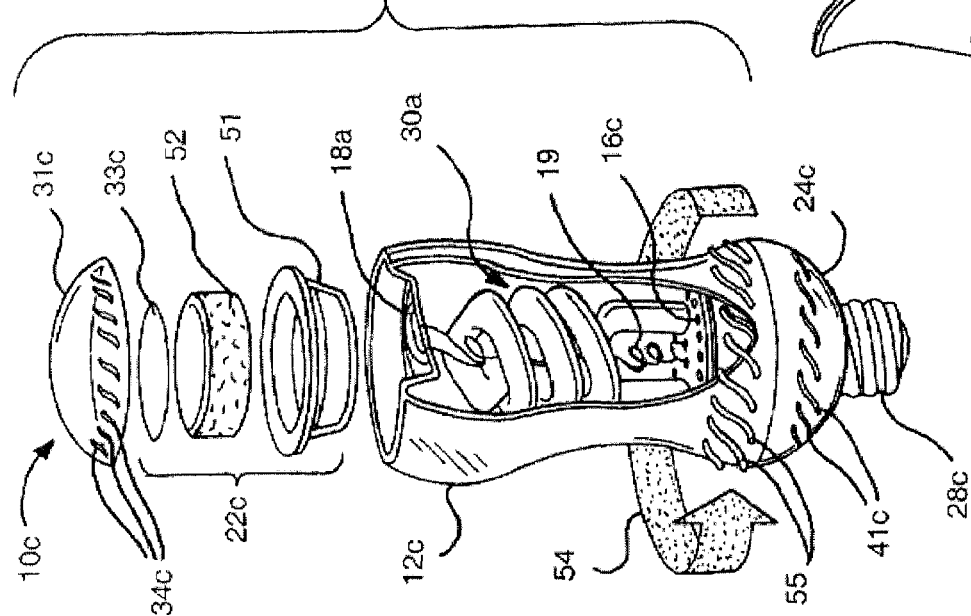
FIG. 15 is a sectional and partially exploded view of the device shown in FIG. 14, particularly illustrating a bowl-shaped volatile active dispenser disposed neat the top of the device and incorporating a cylindrical wick.
Figure 14:
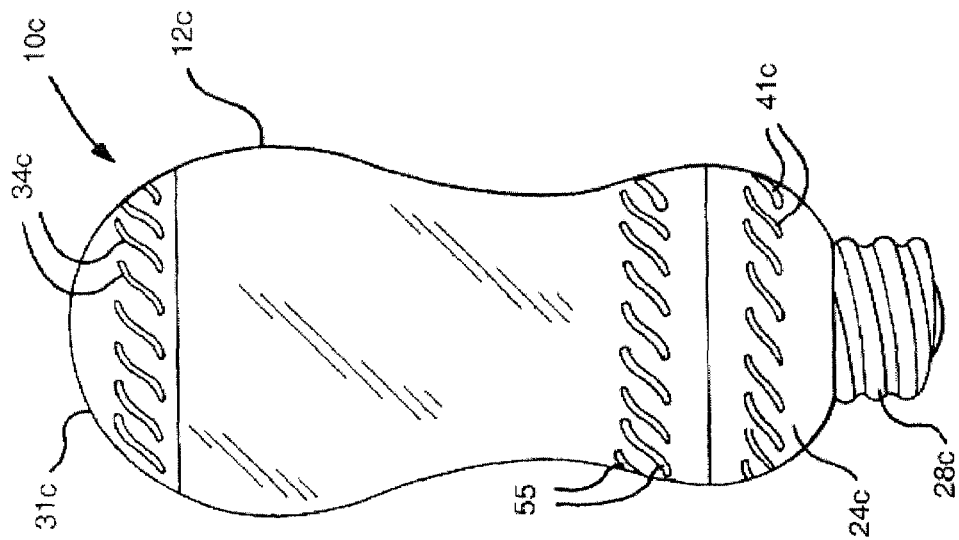
FIG. 14 is an elevational view of yet another combination white light/colored light show/volatile active ingredient emission device made in accordance with this disclosure.

Turning to Figures and 14-16, the embodiment 10*c* includes an outer shell 12*c* with a top 31*c* similar to the embodiment 10*a* of FIG. 6. However the replacement cartridge 22*c* includes a bowl 51 that accommodates the active material as well as a sintered wick 52 and is covered by a permeable membrane 33*c*. The top 31*c* includes a plurality of vents 34*c*. Cooling vents shown at 44*c* are disposed in the lower base 24*c*. In the embodiment 10*c*, the switch mechanism is activated by rotating the housing or shell 12*c* as indicated by the arrow 54. Grips are provided at 55 by the polymeric liner 56 disposed inside the shell 12*c* as illustrated in FIG. 16. Wire connections shown at 19 connect the board 16*c* to the heating element 18*a* disposed in the top of the shell 12*c* as shown in FIG. 15.

The switch mechanism provided by the shell 12*c* rotates the switch (not shown) between the various LED light shows, freeze or pause position, white fluorescent light and the off position. The switch mechanism could also include a booster heater function to increase or decrease the active emission through the 34*c*. Heat vents 41*c* are disposed in the base 24*c*.

Turning to FIGS. 17-19, yet another device 10*d* is disclosed. The device 10*d* includes a shell 12*d* similar to that shown in FIG. 6. The base 24*d* includes an interface toggle switch 35*d* and a curved or c-shaped cartridge 22*d*. The cartridge 22*d* includes a lower moat-shaped reservoir 61 which accommodates active as well as a sintered wick 52*d*. The reservoir 61 is covered with a permeable membrane 33*d* and a cover 31*d* as shown in FIG. 19. The assembly shown in FIG. 19 can be sold as a replacement or refill item.

A finger grip as shown at 55*d* facilitates the insertion and removal of the cartridge 22*d*. A heating element is shown at 18*b* and electrical connectors are shown at 37*d* for purposes of communicating the type of fragrance or active contained within the reservoir 61 to the controller 400. The toggle switch 35*d* includes the same functions discussed above including on/off, scrolling between light shows, freezing the light show and moving between a light show and white fluorescent light. The board 16*d* accommodates a plurality of LEDs shown generally at 14.

The outer shell 12d is of a variable thickness for primarily aesthetic reasons but, however, it will be noted here that an outer shell such as the one shown at 12d can include two walls and itself serve as an active reservoir. Thus, a shell 12 can serve as a replaceable fragrance or active cartridge.

Figure 23:
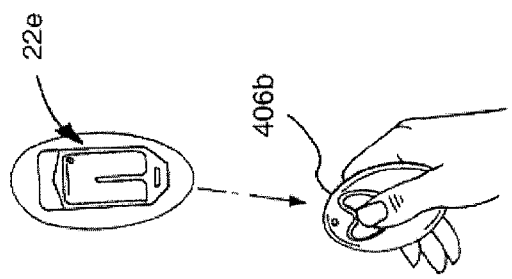
FIG. 23 is a schematic illustration of a remote control device in combination with the replacement active ingredient cartridge that can be adapted for use with any one of the combination devices disclosed herein.
Figure 21:
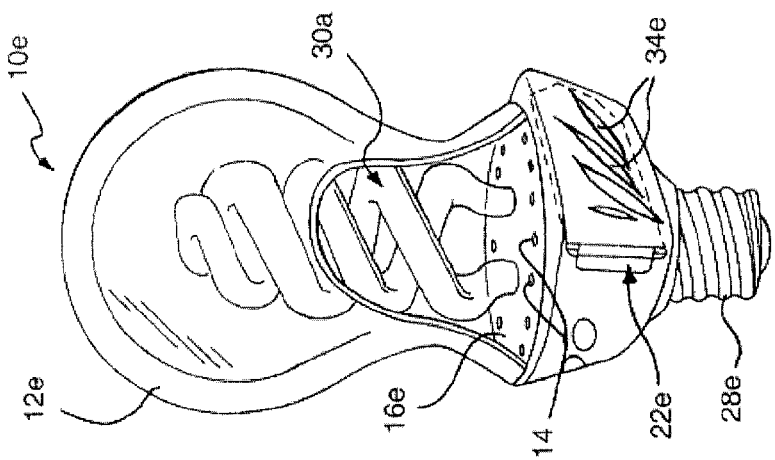
FIG. 21 is a partial sectional and side elevational view of the device shown in FIG. 20.
Figure 20:
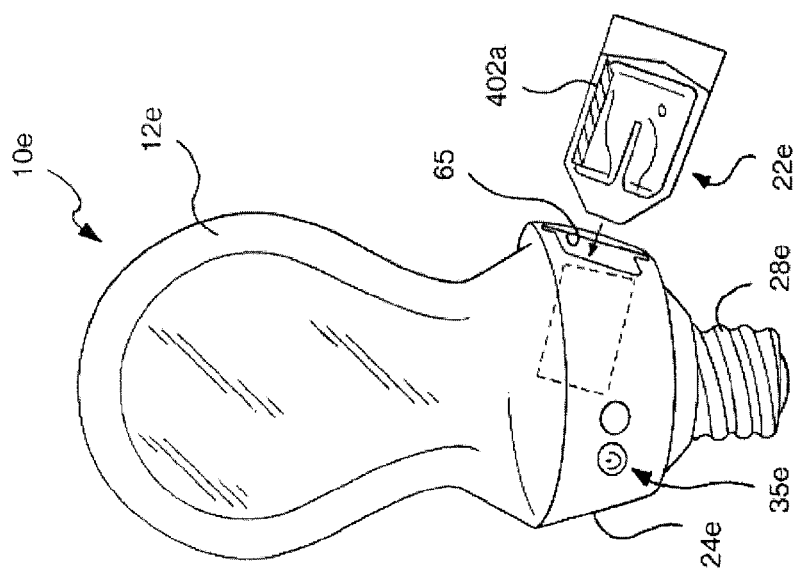
FIG. 20 is a front elevational and partially exploded view of yet another combination white light/colored light show/active ingredient emission device made in accordance with this disclosure and particularly illustrating a replaceable active ingredient cartridge equipped with a programmable chip or memory card with one or more colored light shows stored therein.

Turning to FIGS. 20-23, the device 10e includes a shell 12e that simulates the shape of an incandescent light bulb as other embodiments disclosed above. The shell 12e covers the twisted fluorescent lamp 30a and the board 16e from plain view as its interior surface is frosted. The base 24e includes a two button interface similar to that discussed above in connection with FIGS. 17-19 as well as a slot or compartment shown at 65 for accommodating the replacement active cartridge 22e. The cartridge 22e is equipped with a memory chip or card 402a as shown in FIGS. 20 and 22. This is one scheme for coordinating the light shows with the fragrance are active disposed within the cartridge 22e. In this scheme, the light show is stored on the card or chip 402a and is designed with the fragrance or active disposed within the cartridge 22e in mind. The base 24e may also include a heating element (not shown) for the cartridge 22e. Vapor is emitted through the decorative vents 34 as shown in FIG. 21. FIG. 23 illustrates an embodiment where a remote control 406b is equipped with its own active cartridge 22e which, is discussed above, would be coordinated with the light show or light shows performed at the device 10e.

Figure 24:
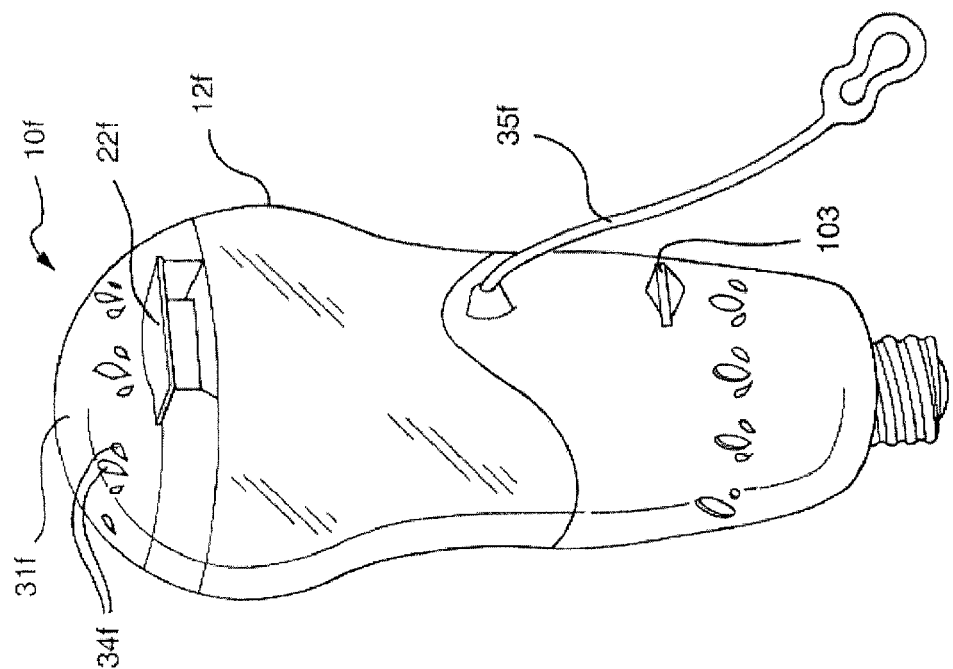
FIG. 24 is an elevational view of a combination white light/colored light show/active ingredient emission device made in accordance with this disclosure particularly illustrating a slot for accommodating a memory card or chip and a lanyard-type on/off switch.
Figures 26, 27:
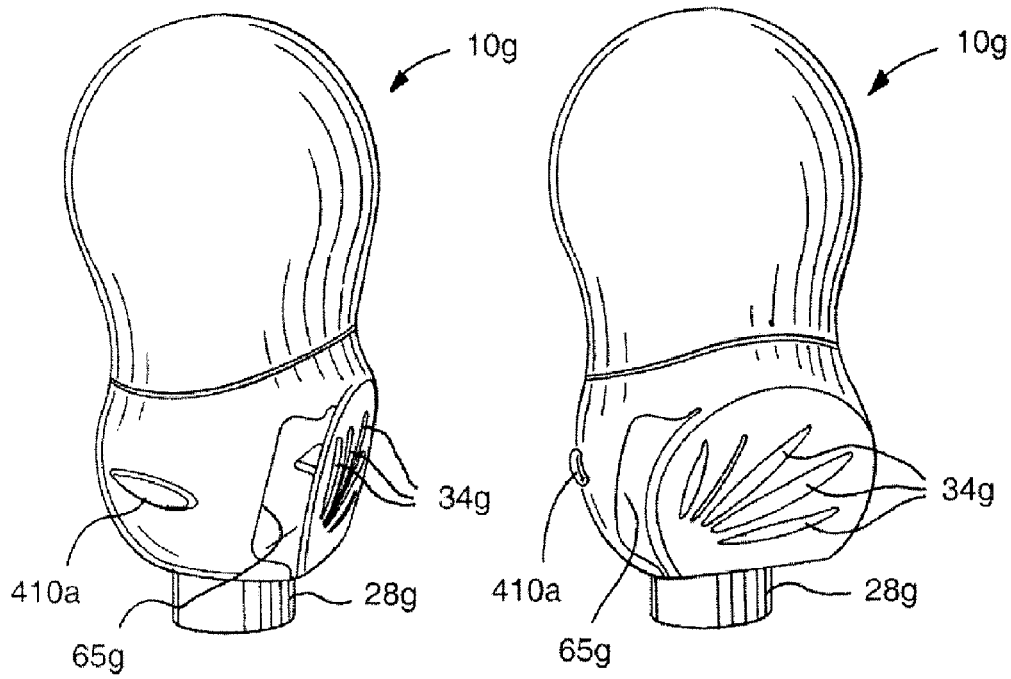
FIGS. 26-35 are various views of other combination white light/colored light show/active ingredient emission devices made in accordance with this disclosure, particularly illustrating the location of an active ingredient cartridge in a slot or compartment disposed in the base and one, two and three button control mechanisms disposed in the bases of the devices.

Turning to FIGS. 24-25, the device 10f is disclosed which includes a shell 12f having a flat top that supports a heater 18c and a volatile active receiving structure 68 that includes a slot or compartment for receiving the fragrance or active cartridge 22f. The cartridge 22f the top 31f that is equipped with decorative vents 34f. Wiring 19f connects the board 16f to the heater 18c. Again, a lanyard-type switch 35f is employed and can provide all the switch functions discussed above with the other devices. A slot 103 is provided for accommodating a memory chip or card 402b is illustrated in FIG. 25.

Finally, turning to FIGS. 26-35, other devices 10g-10k are disclosed which include uniquely shaped outer shells 12g-12k. The bases 24g-24k include from one to three buttons 410a, 410b, 410c which provide the switch functions discussed above. The compartments or slots 65g-65k accommodate a volatile active cartridge (not shown in FIGS. 26-35). Various designs for vents are shown at 34g-34k for releasing fragrance or active vapor in an efficient manner and that further provide aesthetic effects.

Thus, the embodiments described above all look like conventional incandescent light bulbs and can be received in a conventional light socket and serve as a replacement for a conventional light bulb, of the indoor type or outdoor type. Not only can the disclosed devices be used in conventional lamp fixtures and light sockets, the disclosed devices can be useful in closets and used for outdoor lighting purposes as described above. When used outdoors, one suitable combination is colored and white light emission with insect control.

All the devices include fragrance or active ingredient refill cartridges so the user can switch fragrances or active ingredients and coordinate fragrances are active ingredients with the light show of the device. The light shows or colored light themes may be coordinated with volatile active emission as well as light shows or colored light can be used to set the mood when the volatile active is an aromatherapy material, a medicine or medicinal fragrance.

Additional light shows may be supplied by way of memory cards or chips either separate from or in connection with the replacement fragrance or active cartridges. Thus, the consumer can conveniently and inexpensively match the fragrance or volatile active with a LED light show or light theme.

The refill cartridges may be directly connected to the controller or device conducting the LED light show or communication between the memory chip or memory card and the controller can be accomplished through RFID technology as disclosed above at 448 and FIG. 4. Fragrance or active vapor delivery may be constant for each mode or may be varied as heater boost settings may be incorporated into the switch mechanisms for the devices that include a heating element. The heating elements can be designed to mimic the heat generated by a fluorescent bulb (140° F.) to keep a constant delivery of fragrance when the device is used for conventional white light or when the device is used for displaying a light show.

Switch mechanisms can vary greatly from a single switch, a toggle switch, a lanyard-type switch, one, two and three button type interfaces, rotating switches built in to either the base or housing and remote controls. Preferably, the fluorescent lamp is turned off during a LED light show as a LED light show generates light about equivalent to an 8 W night light. Thus, leading the fluorescent lamp on during the LED light show would be counterproductive in terms of enjoying the light show.

In a preferred embodiment, the fluorescent lamp or coiled fluorescent lamp (CFL) is equivalent to a 60 W incandescent light bulb. Typically, it takes two minutes to reach 60 W. The use-up cue function 420 of FIG. 4 may either be a timer device, such as a 30 day timer, or may include a sensor to determine whether a cartridge is actually depleted. In any event, a sound function may be incorporated into the use-up cue.

These figures show only possible arrangements for configuring and controlling the disclosed devices. Many different embodiments may be constructed without departing from the spirit and scope of our invention. It should be understood that disclosure is not limited to the specific embodiments described in this specification. To the contrary, this disclosure is intended to cover various modifications and equivalent air arrangements included within the spirit and scope of this disclosure as defined by the claims. The scope of the claims is to be accorded the broadest interpretation so as to encompass all such modifications, equivalent structures and functions.

INDUSTRIAL APPLICABILITY

The devices of this disclosure makes it possible to achieve an overall desired effect by providing mood lighting, active ingredient emission, and functional white lighting from a single device that resembles a conventional light bulb.

While only certain embodiments have been set forth, alternatives and modifications will be apparent from the above description to those skilled in the art. These and other alternatives are considered equivalents and within the spirit and scope of this disclosure and the appended claims.

What is claimed:

1. A combination light source and volatile active dispenser device, comprising:
    a male base for engaging a light socket, the base being coupled to a light source and supporting a control circuitry and a plurality of colored light sources, the control circuitry comprising a memory with at least one colored light show stored in the memory,
    a replaceable container containing an active material disposed within the base,
    an outer shell connected to the base and enclosing the light source and control circuitry.

2. The device of claim 1 wherein the light source comprises a white light with an intensity level that can be adjusted by the control circuitry.

3. The device of claim 2 wherein the light source further comprises a white light source and the device further comprises at least one switch performing one or more functions selected from the group consisting of:
turning the white light source on; turning the white light source off; activating the light show; deactivating the light show; turning off both the white light source and light show; freezing the light show; selecting a light show from a plurality of light shows stored in the memory; increasing active emission; adjusting the intensity of the white light source; adjusting the intensity of the light show.

4. The device of claim 3 further comprising a remote control to control the switch.

5. The device of claim 1 wherein the light show is dependent upon the active or vice versa.

6. The device of claim 1 wherein the light source comprises a low voltage white light source.

7. The device of claim 1 wherein the light source comprises a plurality of incandescent colored lights.

8. The device of claim 1 wherein the light source comprises a twisted fluorescent lamp and the control circuitry comprises a dimmable electronic ballast.

9. The device according to claim 1, wherein the active ingredient in the active ingredient container is selected from the group consisting of a fragrance, an air sanitizer, an air deodorizer, an insecticide, an insect repellant, an insect attractant, a medicine, an aromatherapy oil, and combinations thereof.

10. The combination of claim 1 wherein the colored light sources comprise a plurality of incandescent colored lights.

11. The combination of claim 1 wherein the white light source comprises a twisted fluorescent lamp and the control circuitry comprises a dimmable electronic ballast.

12. A combination light source and volatile active dispenser, comprising:
a first device comprising a first male base for engaging a light socket, the first device further comprising a female socket and a first housing connecting the first male base to the female socket,
an active dispenser comprising a replaceable container containing vaporizable active material disposed within the first male base,
a second device comprising a second male base mateably received in the female socket of the first device, the second male base being connected to a second housing, the first and second housings enclosing one or more functions selected from the group consisting of a white light source, a plurality of colored light sources, and a control circuitry.

13. The combination of claim 12 wherein the control circuitry comprises a memory with at least one colored light show stored in the memory.

14. The combination of claim 13 wherein the light show is dependent upon the active or vice versa.

15. The combination of claim 13 further comprising at least one switch performing one or more functions selected from the group consisting of:
activating the light show and turning off the white light source; turning on the white light source and deactivating the light show; turning off both the white light source and light show; freezing the light show; selecting a light show from a plurality of light shows stored in the memory; adjusting active emission dispense rate; adjusting white light intensity; and adjusting light show intensity.

16. The combination of claim 15 further comprising a remote control to control the switch.

17. The combination of claim 12 wherein the white light source can be dimmed by the control circuitry.

18. The combination of claim 12 wherein the white light source comprises a low voltage white light source.

19. A combination white light source, light show generator and air treatment device, comprising:
a male base for engaging a light socket, the base being coupled to a white light source and supporting control circuitry and at least one light group comprising a red, green and blue light cluster,
the control circuitry comprising memory for storing a plurality of colored light shows and circuitry for controlling an intensity of the white light source,
a replaceable container containing a volatile active disposed within the base,
an outer shell connected to the base and enclosing the white light source, light group and control circuitry,
at least one switch performing one or more functions selected from the group consisting of
activating the light show and turning off the fluorescent lamp,
turning on the white light source and deactivating the light show,
turning off both the lamp and light show;
freezing the light show;
adjusting the intensity of the white light source; and
scrolling through the plurality of light shows stored in the memory.

* * * * *